US009585987B2

(12) United States Patent
Bergman et al.

(10) Patent No.: US 9,585,987 B2
(45) Date of Patent: Mar. 7, 2017

(54) COMPOSITION FOR THE FORMATION OF GELS

(75) Inventors: Kristoffer Bergman, Stockholm (SE); Tim Bowden, Uppsala (SE); Thomas Engstrand, Uppsala (SE); Jons Hilborn, Sigtuna (SE); Dmitri Ossipov, Uppsala (SE)

(73) Assignee: PVAC MEDICAL TECHNOLOGIES LTD, Nicosia (CY)

( * ) Notice: Subject to any disclaimer, the term of this patent is extended or adjusted under 35 U.S.C. 154(b) by 405 days.

(21) Appl. No.: 12/920,117

(22) PCT Filed: Feb. 13, 2009

(86) PCT No.: PCT/SE2009/000084
§ 371 (c)(1),
(2), (4) Date: Aug. 30, 2010

(87) PCT Pub. No.: WO2009/108100
PCT Pub. Date: Sep. 3, 2009

(65) Prior Publication Data
US 2011/0008444 A1    Jan. 13, 2011

Related U.S. Application Data

(60) Provisional application No. 61/032,662, filed on Feb. 29, 2008.

(30) Foreign Application Priority Data

Mar. 3, 2008    (SE) ...................... 0800506

(51) Int. Cl.
| A61K 31/728 | (2006.01) |
| A61L 27/54 | (2006.01) |
| A61L 24/00 | (2006.01) |
| A61L 24/08 | (2006.01) |
| A61L 27/20 | (2006.01) |
| A61L 27/44 | (2006.01) |
| A61L 27/52 | (2006.01) |
| C08B 37/08 | (2006.01) |
| C08J 3/075 | (2006.01) |
| C08L 5/08 | (2006.01) |
| A61K 31/785 | (2006.01) |
| A61K 31/74 | (2006.01) |

(52) U.S. Cl.
CPC ............ *A61L 27/54* (2013.01); *A61K 31/728* (2013.01); *A61L 24/0015* (2013.01); *A61L 24/0031* (2013.01); *A61L 24/08* (2013.01); *A61L 27/20* (2013.01); *A61L 27/44* (2013.01); *A61L 27/52* (2013.01); *C08B 37/0072* (2013.01); *C08J 3/075* (2013.01); *C08L 5/08* (2013.01); *A61K 31/74* (2013.01); *A61K 31/785* (2013.01); *A61L 2300/602* (2013.01); *C08J 2305/08* (2013.01)

(58) Field of Classification Search
None
See application file for complete search history.

(56) References Cited

U.S. PATENT DOCUMENTS

| 6,303,585 | B1 | 10/2001 | Spiro et al. |
| 6,620,927 | B2 | 9/2003 | Bulpitt et al. |
| 6,630,457 | B1 | 10/2003 | Aeschlimann et al. |
| 6,884,788 | B2 | 4/2005 | Bulpitt et al. |
| 7,196,180 | B2 | 3/2007 | Aeschlimann et al. |
| 2004/0072793 | A1 | 4/2004 | Aeschlimann et al. |
| 2005/0002893 | A1 | 1/2005 | Goldmann |
| 2006/0281912 | A1* | 12/2006 | James et al. ................. 536/53 |
| 2007/0149441 | A1 | 6/2007 | Aeschlimann et al. |
| 2007/0243131 | A1* | 10/2007 | Chen et al. ................. 424/1.11 |
| 2008/0032920 | A1 | 2/2008 | Prestwich et al. |

FOREIGN PATENT DOCUMENTS

| WO | 9901143 A1 | 1/1999 |
| WO | 0078356 A1 | 12/2000 |

(Continued)

OTHER PUBLICATIONS

Jia (Prolongation of aciatic nerve blockade by in situ cross-linked hyaluronic acid, Biomaterials 25 (2004) 4797-4804).*
Ossipov et al. (Formation of the First Injectable Poly(vinyl alcohol) hydrogel by Mixing of Functional PVA Precursors, Applied Polymer Science, vol. 106, 60-70 (2007)).*
International Search Report, dated Apr. 30, 2009, from corresponding PCT application.
Kristoffer Bergman et al., "Hyaluronic Acid Derivatives Prepared in Aqueous Media by Triazine-Activated Amidation", Biomacromolecules, 2007, pp. 2190-2195, vol. 8.

(Continued)

*Primary Examiner* — Ali Soroush
*Assistant Examiner* — Danielle Sullivan
(74) *Attorney, Agent, or Firm* — Young & Thompson

(57) ABSTRACT

A composition, which upon activation, spontaneously forms a cross-linked hydrogel in aqueous liquid, includes:
a) a formulation containing a hyluronan (HA-formulation) which includes a hyaluronan backbone (HA backbone) and a plurality of a reactive substituent group (reactive HA substituent) which i) is directly attached to the HA backbone, and ii) exhibits the reactive HA-group, and
b) a formulation of a homo-multifunctional cross-linking reagent (CLR-formulation) exhibiting a plurality of a reactive group (reactive CLR-group). The two reactive groups are selected as a pair of counterparts that mutually and selectively react with each other to form a linkage structure. The hydrogel contains a cross-linking structure which a) is attached to the hyaluronan via two or more of the linkage structure and is defined by the reagent. The cross-linking structure exhibits a plurality of hydroxyl groups. The composition can be used in vivo or ex vivo as a support matrix.

21 Claims, No Drawings

(56) References Cited

FOREIGN PATENT DOCUMENTS

| WO | 2007120818 A2 | 10/2007 |
| WO | 2008031525 A1 | 3/2008 |

OTHER PUBLICATIONS

Paul Bulpitt et al., "New strategy for chemical modification of hyaluronic acid: Preparation of functionalized derivatives and their use in the formation of novel biocompatible hydrogels", J. Biomed. Mater. Res., 1999, pp. 152-169, vol. 47.
Vittorio Crescenzi et al., "Novel Hydrogels via Click Chemistry: Synthesis and Potential Biomedical Applications", Biomacromolecules, 2007, pp. 1844-1850, vol. 8.
Yon W. Ebright et al., "Incorporation of an EDTA-Metal Complex at a Rationally Selected Site within a Protein: Application to EDTA-Iron DNA Affinity Cleaving with Catabolite Gene Activator Protein (CAP) and Cro", Biochemistry, 1992, pp. 10664-10670, vol. 31.
C.J. Gray et al., "Preparation and properties of some alpha-AZA-amino-acid derivatives, their possible use in peptide synthesis", Tetrahedron, 1977, pp. 739-743, vol. 33.
Anna Gutowska et al., "Injectable Gels for Tissue Engineering", The Anatomical Record, 2001, pp. 342-349, vol. 263.
Sei Kwang Hahn et al., "Sustained released formulation of erythropoietin using hyaluronic acid hydrogels crosslinked by Michael addition", International Journal of Pharmaceutics, 2006, pp. 44-51, vol. 322.
Allan S. Hoffman, "Hydrogels for biomedical applications", Advanced Drug Delivery Reviews, 2002, pp. 3-12, vol. 43.
Jeffrey A. Hubbell, "Synthetic biodegradable polymers for tissue engineering and drug delivery", Current Opinion in Solid State & Materials Science, 1998, pp. 246-251, vol. 3.
Xinqiao Jia et al., "Hyaluronic Acid-Based Microgels and Microgel Networks for Vocal Fold Regeneration", Biomacromolecules, 2006, pp. 3336-3344, vol. 7.
Xinqiao Jia et al., "Prolongation of sciatic nerve blockade by in situ cross-linked hyaluronic acid", Biomaterials, 2004, pp. 4797-4804, vol. 25.
Xinqiao Jia et al, "Synthesis and Characterization of in Situ Cross-Linkable Hyaluronic Acid-Based Hydrogels with Potential Application for Vocal Fold Regeneration", Macromolecules, 2004, pp. 3239-3248, vol. 37.
Jungju Kim et al., "Bone regeneration using hyaluronic acid-based hydrogel with bone morphogenic protein-2 and human mesenchymal stem cells", Biomaterials, 2007, pp. 1830-1837, vol. 28.
Gun-Woo Kim et al., "Synthesis and evaluation of hyaluronic acid-poly(ethylene oxide) hydrogel via Michael-type addition reaction", Current Applied Physics, 2007, pp. e28-e32, vol. 7S1.
Kelly R. Kirker et al., "Glycosaminoglycan hydrogel films as bio-interactive dressings for wound healing", Biomaterials, 2002, pp. 3661-3671, vol. 23.
Kelly R. Kirker et al., "Physical Properties of Glycosaminoglycan Hydrogels", Journal of Polymer Science: Part B: Polymer Physics, 2004, pp. 4344-4356, vol. 42.
Kuen Yong Lee et al., "Hydrogels for Tissue Engineering", Chemical Reviews, Jul. 2001, pp. 1869-1879, vol. 101, No. 7.
Yi Luo et al., "Cross-linked hyaluronic acid hydrogel films: new biomaterials for drug delivery", Jounal of Controlled Release, 2000, pp. 169-184, vol. 69.

Dmitri Ossipov et al., "Formation of the First Injectable Poly(vinyl alcohol) Hydrogel by Mixing of Functional PVA Precursors", Journal of Applied Polymer Science, 2007, pp. 60-70, vol. 106.
Dimitri Ossipov et al., "Poly(vinyl alcohol) Cross-Linkers for in Vivo Injectable Hydrogels", Macromolecules, 2008, pp. 3971-3982, vol. 41.
Yong Doo Park et al., "Photopolymerized hyaluronic acid-based hydrogels and interpenetrating networks", Biomaterials, 2003, pp. 893-900, vol. 24.
Glenn D. Prestwich et al., "3-D culture in synthetic extracellular matrices: New tissue models for drug toxicology and cancer drug discovery", Advances in Enzyme Regulation, 2007, pp. 196-207, vol. 47.
Johann M.G. Reyes et al., "A Modified Chondroitin Sulfate Aldehyde Adhesive for Sealing Corneal Incisions", Investigative Ophthalmology & Visual Science, Apr. 2005, pp. 1247-1250, vol. 46, No. 4.
Cleo M. Salisbury et al., "Peptide Microarrays for the Determination of Protease Substrate Specificity", J. Am. Chem. Soc., 2002, pp. 14868014870, vol. 124.
Rachael H. Schmedlen et al., "Photocrosslinkable polyvinyl alcohol hydrogels that can be modified with cell adhesion peptides for use in tissue engineering", Biomaterials, 2002, pp. 4325-4332, vol. 23.
Daniel Schwartz et al., "Integrity and stability studies of precipitated rh BMP-2 microparticles with a focus on ATR-FTIR measurements", European Journal of Pharmaceutics and Biopharmaceutics, 2006, pp. 241-248, vol. 63.
Xiao Zheng Shu et al., "Disulfide Cross-Linked Hyaluronan Hydrogels", Biomacromolecules, 2002, pp. 1304-1311, vol. 3.
Xiao Zheng Shu et al., "In situ crosslinkable hyaluronan hydrogels for tissue engineering", Biomaterials, 2004, pp. 1339-1348, vol. 25.
Xiao Zheng Shu et al., "Attachment and spreading of fibroblasts on an RGD peptide-modified injectable hyaluronan hydrogel", J. Biomed. Mater. Res., 2004, pp. 365-375, vol. 68A.
Xiao Zheng Shu et al., "Synthesis and evaluation of injectable, in situ crosslinkable synthetic extracellular matrices for tissue engineering", J. Biomed. Mater. Res., 2006, pp. 902-912, vol. 79A.
Janssen L. Vanderhooft et al., "Synthesis and Characterization of Novel Thiol-Reactive Poly(ethylene glycol) Cross-Linkers for Extracellular-Matrix-Mimetic Biomaterials", Biomacromolecules, 2007, pp. 2883-2889, vol. 8.
Shyni Varghese et al., "Hydrogels for Musculoskeletal Tissue Engineering", Adv. Polym. Sci., 2006, pp. 95-144, vol. 203.
Michel Wathier et al, "Dendritic Macromers as in Situ Polymerizing Biomaterials for Securing Cataract Incisions", J. Am. Chem. Soc., 2004, pp. 12744-12745, vol. 126.
Robert J. Wood et al., "Optimized Conjugation of a Fluorescent Label to Proteins via Intein-Mediated Activation and Ligation", Bioconjugate Chem., 2004, pp. 366-372, vol. 15.
Ping Xu et al., "Synthesis of PNA Monomers and Dimers by Ugi Four-Component Reaction", Department of Medicinal Chemistry, School of Pharmaceutical Sciences, Peking University Health Science Center, Beijing 100083,P.R. China, Jan. 7, 2003 and revised Mar. 3, 2003, p. 1171-1176.
Yang Shoufeng et al. "The Design of Scaffolds for Use in Tissue Engineering", Part I. Traditional Factors, Tissue Engineering, vol. 7, No. 6, 2001, Mary Ann Liebert , Inc., p. 679-689.
Extended European Search Report, dated Mar. 25, 2013, from corresponding EP application.

\* cited by examiner

COMPOSITION FOR THE FORMATION OF GELS

TECHNICAL FIELD

The present invention relates to a composition which can be used for in situ formation of hydrogels based on hyaluronan. Gel formation may take place in vivo or ex vivo. The invention also comprises the use of the gels as support matrices/extracellular matrices (ECM) for a) tissue generation including both tissue regeneration and tissue engineering, b) sustained release of a bioactive substance that is incorporated in the gel (vehicle), c) cosmetic surgery, d) tissue gluing, e) tissue separation, f) immunizations with the immunogen incorporated in the gel (adjuvant) etc. Ex vivo uses encompass for instance use of the gels as a support matrix in cell and/or tissue culturing. The invention also comprises a method for producing hylauronan-based hydrogels ex vivo or in vivo.

The invention is based on cross-linking of a hyaluronic acid derivative (a hyaluronan or HA) which exhibits a plurality of a reactive group by the use of a cross-linking reagent (CLR) which exhibits a plurality of another reactive group. The two reactive groups define a pair of groups which are mutually and selectively capable of reacting with each other to the formation of a linkage structure, preferably covalent. Reactive groups of this kind of pair will be called reactive counterparts, counterpart groups, counterparts etc and will include protected forms (inactive forms) of the groups if not otherwise indicated by the context. Protected forms may be transformed/activated to active forms. For a hyaluronan exhibiting a member of this kind of reactive pair in an aqueous liquid, the reaction between counterparts applied to the field of the invention means formation of a cross-linked hyaluronan hydrogel in which the structure of a crosslink will comprise a CLR structural element flanked by linkage structures formed by reaction of reactive groups that are counterparts. The CLR element will derive from parts of the cross-linking reagent located between its reactive groups. The two members of a pair of counterparts when present on a hyaluronan and a cross-linking reagent will be called reactive HA-group and reactive CLR-group, respectively.

The terms "plurality", "multi" and "poly" will contemplate two, three, four, five or more if not otherwise indicated.

BACKGROUND TECHNOLOGY

All publications, in particular US patents and patent applications, cited in this specification are incorporated by reference in their entirety.

Biodegradable materials which are useful as temporary artificial ECMs have been developed over the past decades (Yang et al *Tissue Engineering* 2001 7(6) 679-689). Their usefulness rely among others on their biocompatability and resemblance to natural ECMs (Hoffmann, *Advanced Drug Delivery Reviews* 2002 54(1) 3-12).

Prestwich et al. pioneered modification of HA by thiolation (Shu et al *Biomacromolecules* 2002 3 1304-1311) making it capable to cross-link with PEG diacrylate (Shu et al *Biomaterials* 2004 25 1339-1348) or PEG bis-maleimide (Vanderhooft et al *Biomacromolecules* 2007 8 2883-2889) for in situ production of hydrogel scaffolds that are degraded by hyaluronidase. Gelation of thiolated HA with RGD-peptide containing tri-block acrylate-PEG-CC(PEG-acrylate) RGDS cross-linker (Shu. et al *Biomed Mater. Res.* 2004, 68(A) 365-375) or combination of thiol-modified HA with thiol-modified gelatin (Shu et al J. *Biomed. Mater. Res.* 2006 79(A) 902-912; and Prestwich et al *Advan. Enzyme Regul.* 2007 47 196-207) allowed to construct cytoadherent synthetic ECM mimics for tissue engineering. An alternative functionalization, when electrophilic acrylate groups are localized on HA, whereas the sulfhydryl groups on PEG (Kim et al *Current Applied Physics* 2007, 7(S1) e28-e32; and Kim et al *Biomaterials* 2007 28 1830-1837) or bis-cysteine peptide cross-linker (Hahn et al *Int. J. Pharm.* 2006 322 44-51) was also examined for hydrogel preparation by Michael addition. Formation of reversible thiazolidine cross-linkages between cysteine 1,2-aminothiol terminated dendron and PEG dialdehyde was used to render a hydrogel that stays intact for approximately one week after preparation (Wathier et al *J. Am. Chem. Soc.* 2004 126 12744-12745). Finally hydrazone formation is one of a few other examples of cross-linking chemistries that were suggested for in vivo production of hydrogel materials (Luo et al *J. Control. Release* 2000 69 169-184; Kirker et al *J. Polym. Sci. Part B* 2004 42 4344-4356; and Kirker et al *Biomaterials* 2002 23 3661-3671). Thus, both hydrolytically (due to hydrolysis of hydrazone linkages) and enzymatically degradable hydrogels were prepared from hydrazide-modified HA and PEG dialdehyde (Luo et al *J. Control. Release* 2000, 69, 169-184; and Kirker et al *J. Polym. Sci. Part B* 2004, 42, 4344-4356) and used for wound healing (Kirker et al *Biomaterials* 2002 23 3661-3671).

A limited number of cross-linkers with suitable reaction kinetics are available for preparation of hydrogels, e.g. by changing the reactivity of thiophilic bis-functional cross-linkers (Vanderhooft et al *Biomacromolecules* 2007, 8, 2883-2889). Another approach is the use of multifunctional cross-linkers which was recently realized for HA by its modification into two HA derivatives comprising side chains terminated with electrophilic aldehyde and nucleophilic hydrazide chemoselective functionalities respectively (Bulpitt et al Aeschlimann, D. *J. Biomed. Mater. Res.* 1999 47 152-169; Jia et al *Biomaterials* 2004, 25, 4797-4804; and Jia et al *Biomacromolecules* 2006 7 3336-3344. This topic has also been investigated by us (Ossipov et al *J. Appl. Polymer Sci.* 2007 106 60-70).

Other examples of publications dealing with the field of the invention are Aeschlimann et al. (U.S. Pat. No. 7,196, 180; U.S. Pat. No. 6,630,457 and US 20070149441; Bulpitt et al. U.S. Pat. No. 6,620,927 and U.S. Pat. No. 6,884,788; Park et al *Biomaterials* 24 (2003) 893-900; Spiro et al U.S. Pat. No. 6,303,585; and Crescenzi et al *Biomacromolecules* (2007 No 8 1844-1858).

Formation of hydrogels in situ by cross-linking synthetic polyhydroxypolymers by the use of homo-multifunctional cross-linking reagents that comprises non-biopolymer structure has also been reported (Ossipov et al *J. Appl. Polymer Sci.* 2007 106 60-70; Schmedlen et al *Biomaterials* 2002 23 4325-4332; and Reyes et al *Ophthalmology & Visual Sci.* 2005 46(4) 1247-1250.

A search performed by the Swedish Patent Office with respect to the SE priority application has cited Prestwich et al (US 20080032920) which deals with hydrogel formation by reacting a thiolated macromolecule with an α-halo carbonyl modified macromolecule.

Unfavourable results with respect to biocompatability have been reported for amino-derivatized hyaluronic acid cross-linked with an uncharacterized aldehyde-modified dextran (Bulpitt et al *J. Biomed. Mat. Res.* 47(2) (1999) 152-169).

Bergman et al (Biomacromolecules 8(7) (2007) 2190-2195) have reported about the versatility of triazine activation of the carboxy group of hyaluronic acid.

Objectives

Hydrogels that are formed in situ from polymeric networks based on cross-linking of multifunctional polymers should be implantable by minimally invasive surgery. Such polymers including precursors of the network should thus be possible to administer through syringes, e.g. by injection. This mode of administration typically requires that the precursor reagents during the administration are present as a mixture in a liquid media which should have viscosity that is low enough to permit easy administration through a syringe used and enabling the liquid to easily fill complex shaped areas with good contact for the formed hydrogel to the native tissue. Cells and/or bioactive substances, such as therapeutic agents, should easily be able to penetrate or be encapsulated in the formed gel See for instance Gutowska et al *Anatomical Record* 2001 263(4) 342-349; Vargese et al *Adv. Polym. Sci.* 2006 203 (*Polymers for regenerative medicine*) 95-144; Hubbell et al *Curr. Opin. Solid State and Mat. Sci.* 1998 3 246-251; and Lee et al *Chem. Rev.* 2001 101(7) 169-1879. Similar viscosity criteria apply to the handling of individual formulations of precursor reagents (HA and CLR). In general the viscosity should be low enough to permit quick mixing of the components/reagents in order to achieve rapid cross-linking and hydrogel formation.

Several requirements must be fulfilled for multifunctional polymer systems to be used for the in situ formation of hydrogels by cross-linking in vivo. The systems have to be biocompatible after implantation of the hydrogel, which in addition to biocompatibility of the hydrogel as such means that a) precursor compounds should have the ability to crosslink in vivo without forming toxic by-products, and b) degradation products from the polymeric network of the hydrogel have to be harmless. Cross-linking should take place by utilizing addition reactions and/or substitution reactions and/or elimination reactions each of which should release no or only harmless molecules (e.g. $H_2O$ and molecules which as such may be harmful but whose negative effects easily and quickly can be neutralized in vivo). The use of reactants other than the polymer to be cross-linked and the cross-linking reagent should be avoided both from a practical point of view and the fact that such agents also would imply biocompatability requirements similar to those applicable to the starting basic components, i.e. in our case the hyaluronan and the cross-linking reagent. The cross-linking reactions should be selective and appear at a high rate leading to gel formation within less than some minutes (typically less than a minute or two) and yet allow for sufficient mixing of the components (Ossipov et al *J. Appl. Polymer Sci.* 2007 106 60-70). The gels should be degradable in vivo at a rate that often varies for different applications and effects to be achieved, for instance for a) different tissue regenerations and encapsulated grow factors, b) different immunogens and immunization protocols, c) different tissues to be glued and gluing protocols, d) different bioactive substances, such as drugs or other therapeutic agents, e) to have local and/or systemic effects etc. Thus it is desirable with polymeric systems for which it is possible to control the cross-linking degree as well as the rate of degradation in vivo of the hydrogels, for instance by varying kind, molecular weight and concentration of starting components, kind of reactive functional groups and their concentration in the mixture to be administered, relative amount of reactive counterparts, i.e. (total amount of reactive HA-groups)/(total amount of reactive CLR-groups), degree of substitutions with respect to (content of) reactive HA-group and reactive CLR group in the hyaluronan and the cross-linking reagent, respectively, etc.

The use in vivo of gels based on synthetic polymers and other non-endogenous polymeric materials is restricted by the risk of bio-incompatability, i.e. the risk of eliciting a negative body response, for instance inflammatory and anaphylactic responses of either immunological or non-immunological origin. The level of such responses for the gels as such and precursor reagents should be kept at an acceptable level or at a level not observable in test models and systems as is well-known in the literature. Thus infiltration of inflammatory cells, including giant cells and lymphocytes, should be insignificant, i.e. be void or non-indicative of chronic inflammation. In vitro cytotoxicity tests should show insignificant cytotoxicity.

A general objective and challenge thus is to provide polymer based systems for in situ formation of hydrogels meeting one or more of the above-mentioned requirements.

The Invention

The present inventors have realized that the above-mentioned challenge at least partly can be coped with by using a cross-linking reagent which provides a cross-linking structure which exhibits a plurality of hydroxyl groups and is devoid of hyaluronan structure.

In one of its main aspects (first aspect) the present invention thus is a composition containing a hyaluronan-formulation (HA-formulation) and a formulation of a homo-multifunctional cross-linking reagent (CLR-formulation) which is devoid of hyaluronan structure and provides a plurality of hydroxyl groups in the cross-linking structure introduced by the reagent. The hyaluronan of the HA-formulation is cross-linkable by the use of the homo-multifunctional cross-linking reagent. Plurality for number of hydroxy groups in the cross-linking reagent and/or cross-linking structure preferably mean≥5 or ≥10. The composition is activatable in the sense that the cross-linking reagent and the hyaluronan are initially unreactive towards each other but upon activation of the composition cross-linking spontaneously starts in an aqueous liquid with formation in situ of the hydrogel. The aqueous liquid contains at the start of the cross-linking (=end of activation) active forms of both the hyaluronan and the cross-linking reagent. The cross-linking reaction is a selective reaction between a reactive functional group of the cross-linking reagent and a reactive functional group of the hyaluronan. The two reactive groups are counterparts to each other as defined above (reactive CLR-group and reactive HA-group, respectively).

A characterizing feature of preferred variants of the composition is that it comprises:
A) a HA-formulation in which the hyaluronan exhibits the carbohydrate backbone of native hyaluronic acid (HA-structure/HA-backbone) and a plurality of a reactive substituent (reactive HA-substituent) which
  i) is directly attached to the HA-backbone,
  ii) exhibits a reactive HA-group as defined above, and
B) a CLR-formulation containing a multi-homofunctional polyhydroxy-containing cross-linking reagent, which comprises a plurality of a reactive CLR-group as defined above.

The reactive HA-group is absent in native hyaluronic acid. The cross-linking reagent is devoid of hyaluronan structure, i.e. has a backbone structure that is different from the backbone structure of native hyaluronic acid.

The cross-linking reagent is in preferred variants a polyhydroxy polymer (PHP) which comprises a backbone structure (PHP-backbone) and a plurality of the reactive CLR-substituent which is directly attached to the PHP-backbone and exhibits the reactive CLR-group. The abbreviation PHP will be used instead of CLR for variants in which the cross-linking reagent imperatively is a polyhydroxypolymer.

The hyaluronan and the cross-linking reagent are preferably water-soluble, e.g. at physiologically acceptable pH conditions as defined elsewhere in this specification and at a temperature within the interval of 15-45° C., possibly together with a buffer. This in particular applies to forms of the reagents in which the reactive counterparts are in active form, e.g. lacking protecting groups.

With respect to biocompatibility the composition is characterized in that the hyaluronan and the cross-linking reagent have been selected so that the hydrogel formed as a consequence of activation and cross-linking is biocompatible by complying with the general rules outlined under the heading "Objectives". Thus a gel produced according to the invention that is devoid of a bioactive stubstance of the types described herein as additive should be characterized in giving an acceptable response with respect to foreign body giant cell reaction indicative of chronic inflammation in the in vivo experiments used by Bulpitt et al. (*J. Biomed. Mat. Res.* 47(2) (1999) 152-169) and/or by us in the experimental part of this specification. Thus, infiltration of inflammatory cells, including giant cells and/or lymphocytes, should preferably be unobservable. Cytotoxicity, for instance measured in vitro as done in the experimental part, should be insignificant, e.g. within ±75%, such as ±50%, of the value obtained for the controls (that should be of the same kind as in our experimental part).

Biocompatability of the kinds discussed in the preceding paragraph will depend on factors controlling penetratability of the formed gel by inflammatory cells with a high penetratability permitting more infiltration. The cross-linking degree and groups/structures of the final gel are for instance of importance. Thus by proper selection of kind and amount of cross-linking reagent and its reactive CLR-groups in relation to the hylauronan and its reactive HA-groups the above-mentioned biocompatibility can be accomplished. Testing/screening for appropriate combinations of reagents is done in the model systems given.

An alternative or a complement to the above-mentioned kind of biocompatability is an official approval issued by an ethical committee at a university, hospital and the like and/or by a regulatory authority in one, two or more countries selected amongst the US, JP, EPO-countries for using a gel produced according to the invention in testing in animals, such as humans, and/or in therapy. EPO-countries of importance are Great Britain, the Netherlands, Belgium, France, Spain, Portugal, Italy, Switzerland, Austria, Luxembourg, Germany, Sweden, Denmark, Finland etc.

The HA-formulation and the CLR-formulation of the inventive composition shall support suitable conditions for quick cross-linking and in situ hydrogel formation within given time frames in the aqueous solution resulting from the activation of the composition. Suitable time frames as measured in vitro according to the method given in the experimental part are ≤15 minutes, such as ≤10 minutes with preference for ≤5 or ≤4≤3 minutes and with the highest preference for ≤2 or ≤1 minute. The lower end of these intervals is typically 5 seconds or 10 seconds or 15 seconds.

Useful desired elastic modulus values (shear storage modulus, G') of suitable hydrogels will depend on the intended application and can therefore be found in a broad interval, such as 10 Pa to 1 MPa, most likely with preference for 100 Pa to 10 kPa. Measurement is according to the method given in the experimental part.

Values for the swelling ability of suitable cross-linked hyaluronans hydrogels will depend on the intended application and can therefore be found in a broad interval, such as ≥0%, e.g. ≥10%, and/or ≤10000%, e.g. ≤1000%. Measurement is according to the method given in the experimental part.

Testing/screening for suitable cross-linking conditions that will give hydrogels having gelation times, elastic modulus, and swelling ability that fit predetermined values within the intervals given can be carried out in vitro by methods given in the experimental part. In this kind of screening, parameters that are tested can be selected amongst pH, cross-linking reagents (kind and type), pairs of reactive counterparts including degrees of substitution, total and/or relative concentrations, size and form (e.g. Mw) of hyaluronan and/or cross-linking reagent etc. Screening/testing means that two or more experiments that differ with respect to at least one parameter are carried out and the results compared in order to determine favourable conditions.

Suitable rates of disappearance (resorbability, degradation) of the gel in vivo will depend highly on the particular application and will thus be found within a wide interval, for instance between 1-2 days up to a year for the gel to fully disappear. Thus in the case of cosmetic surgery it may be beneficial for the individual undergoing the treatment if the gel disappears/is resorbed within 2-24 months or a longer period of time with preferred values being less than 12 months. For medical treatments the gel should remain until the effect desired for the dose given has been accomplished. For tissue generations this means as long as it takes for the desired generation to occur and/or if a bioactive substance is incorporated in the gel as long as there is active substance in the gel and/or the desired effect for the dose given has been accomplished. As a general guideline suitable gels can be found amongst those gels which when prepared in vivo as a consequence of subcutaneous or intramuscular injection in rats of an activated composition according to the invention will be retrievable at the location for the administration for a period of time that is within the interval of 1 day to 12 months, such as ≥1 week or ≥1 month or/or ≤8 months or ≤6 months with measurements taking place in the animal model as given in the experimental part including doses given.

Screening/testing for gels giving appropriate disappearance/resorption rates for a desired application is carried by use of the animal model used in the experimental part with screening parameters being in principle the same as for the above-mentioned in vitro screening.

Activation of the Composition, Cross-Linking and Hydrogel Formation

A reactive CLR-group and/or a reactive HA-group may be present in the composition in protected (=activatable/inactive) form or in active form, where protected form means that the group can be transformed (=activated) to the active form which reacts with its counterpart (if in active form) to form the above-mentioned linkage structure. The term "protected" is used in a broad sense and encompasses a) physical separation of the hyaluronan and the cross-linking reagent from each other, and also b) chemical protection, i.e. the reactive group comprises one or more chemical groups that hinder the cross-linking reaction (=protecting groups). Alternative (a) comprises e.g. that the HA- and the CLR-formulations are present in different compartments of the composition or in separate physical states, for instance different powder forms and different other dry or dehydrated forms. In the latter case the two formulations may be present in the same compartment of the composition. Typical chemical protecting groups used in alternative (b) are well-known in synthetic chemistry and are typically removable under mild conditions only affecting desired parts of the reagent carrying the protected group. Typical deprotecting conditions useful for the invention encompass for instance changes in pH, temperature, ionic strength etc and may include an increase in the concentration of a particular anion, such as an anionic nucleophile, or a particular cation, such as a cationic electrophile, and neutral nucleophiles and electrophiles. Proper matching of changes in conditions with the protecting group to be removed is normally required.

The hyaluronan and the cross-linking reagent of the composition are upon activation forming the hydrogel in situ by the cross-linking reaction in the aqueous liquid. In variants utilizing cross-linking reagents that are polyhydroxypolymers the cross-linking structure will exhibit a PHP-backbone.

Activation of the composition comprises transforming reactive HA-groups and reactive CLR-groups that are in protected form in the composition to active forms thereof. Both the hyluronan and the cross-linking reagent will be present in active and dissolved form in a common aqueous solution leading to spontaneous cross-linking of the hyaluronan and formation of the hydrogel in situ via the cross-linking. The transformation typically includes one or more steps:

i) transferring the hyaluronan and the cross-linking reagent, if they are present in separate compartments of the composition, to a common aqueous liquid providing dissolving conditions for both the hyaluronan and the cross-linking reagent, and/or ii) dissolving any reactant selected amongst the hyaluronan and the cross-linking reagent that is in solid form (e.g. powder form, dehydrated form, dry form etc) in an aqueous liquid providing dissolving conditions for the reactant, and/or iii) removing a protecting group that possibly is present in a reactive HA-group or in a reactive CLR-group in an aqueous liquid providing conditions for the removal of the protecting group.

Different combinations of steps (i)-(iii) are possible depending on the particular formulations of the hyaluronan and the cross-linking reagent including presence or absence of protecting groups. In preferred variants, for instance, the hyaluronan and the cross-linking reactant are present in dissolved form in separate aqueous liquid aliquots that in turn are present in different compartments of the composition. The final step in the activation is then provided by mixing the aliquots. If any of the hyaluronan and the cross-linking reactant exhibits a reactive counterpart that comprises a protecting group, the mixed liquid should preferably also provide conditions for the removal of such a protecting group, for instance if the removal is pH-dependent such as for protonated amino-containing groups or COOH/COO$^-$-containing groups.

For compositions adapted for cross-linking and in situ formation of the hydrogel to take place in vivo, the activation should end up in an aqueous liquid containing the two counterpart groups in active forms and providing acceptable conditions for cross-linking as well as for the individual to which the composition is to be administered as discussed elsewhere in this specification.

Reactive Counterpart Groups

The pair of two reactive counterparts and their presence on the hyaluronan and on the cross-linking reagent is selected such that reaction between the two groups during the cross-linking conditions applied will be selective in the sense that linkage structures will preferentially be formed between a reactive HA-group and a reactive CLR-group. The hyaluronan therefore is devoid of counterparts to the reactive HA-groups and the cross-linking reagent is devoid of the counterparts to the reactive CLR-groups. The term "selective" also includes that each of the two counterparts are reacting without significant formation of by-products from competing reactions. In preferred variants there is no need for reagents other than the hyaluronan and the cross-linking reagent, except for buffer systems that may act as deprotection/activation agents by changing the degree of protonation of groups that are to be utilized in the cross-linking.

Reactive HA-groups and reactive CLR-groups should not to any significant degree be counterparts to hydroxy during the cross-linking conditions. This typically means that ≥25%, such as ≥50% or ≥75% or ≥95%, of the reactive HA-groups and/or the reactive CLR-groups are reacting with each other in the intended manner during cross-linking conditions.

The ratio between the molar amount ($M_{HA}$) of the reactive HA-group in the HA-formulation and the molar amount ($M_{CLR}$) of the reactive CLR-group in the CLR-formulation, i.e. the ratio $M_{HA}/M_{CLR}$, is typically within the interval of 0.1-10, such as 0.25-4 or 0.5-2, with preference for essentially in equimolar amounts, i.e. 0.75-1.30 or 0.9-1.1. Ratios deviating from equimolarity may be useful in certain variants of the invention, such as when it is desirable to speed up the consumption of a slow-reacting counterpart or to produce a hydrogel which carries reactive groups (either reactive HA- or reactive CLR-groups). Excessive amounts of a reactive counterpart group may be used for immobilizing a bioactive substance of the kind discussed herein to the hydrogel. Such a bioactive substance shall exhibit a reactive group that is counterpart to the reactive group in excess.

The reaction sequence leading to the above-mentioned linkage structure, which preferably is covalent, preferably comprises a substitution reaction step and/or an addition reaction step, possibly combined with a subsequent elimination reaction step. Ring-forming steps may be included, for instance as a cyclization step subsequent to an elimination step or as an addition step (cycloaddition). Sequences comprising one or more of these steps are preferred since it is often possible to select reactive counterparts that are of sufficient reactivity and selectivity for quick formation of the desired cross-linkages with a minimum formation of harmful by-products as discussed in the objectives above.

In one type of reaction sequence either the reactive HA-group or the reactive CLR-group comprises a nucleophilic group while the remaining one of the two counterparts comprises an electrophilic group.

A nucleophilic counterpart typically comprises a first heteroatom O, N, or S (=X) exhibiting a free electron pair with 0-3 hydrogen attached to the heteroatom and one, two or three organic groups being directly bound to the heteroatom. The organic group typically provides a carbon or a second heteroatom O, N and S directly attached to the first heteroatom X, with the proviso that the second heteroatom should be O, N or S when X=N or S, and N or S when X=O. The preferred nucleophilic counterparts are uncharged during cross-linking. For a nucleophilic counterpart which is a base in an acid-base pair, ≥5%, such as ≥25% or ≥50 or ≥75%, of the total concentration of the acid-base pair should be in base form.

An electrophilic counterpart typically comprises an electron-deficient carbon. In preferred variants the electron-deficient carbon is part of a multiple bond between a) two carbons, or b) between one carbon and one heteroatom selected amongst N, O and S. For addition reactions involving formation of a bond between a nucleophilic counterpart (XH) and an electron-deficient double-bonded carbon, this latter carbon typically carries only hydrogen and/or carbon (i.e. single-bonded to the double-bonded carbon). If the multiple bond contains no heteroatom (i.e. is the double-bonded carbon is part of a carbon-carbon double bond) an electron-withdrawing substituent is typically replacing the single-bonded carbon attached to the electron-deficient carbon (i.e. the electron-withdrawing substituent either comprises the single-bonded carbon or a heteroatom attached directly to the electron-deficient double-bonded carbon). In these addition reactions X of the nucleophilic group (XH) becomes bonded to the electron deficient atom of the multiple bond and hydrogen (H) to the other atom of the multiple bond. For substitution reactions with a nucleophilic counterpart at an electron-deficient double-bonded carbon a suitable leaving group has to be present on the carbon. Preferably the other atom of the double bond is then a double-bonded heteroatom O, S or N. During these substitution reactions the nucleophilic counterpart will displace the leaving group on the electron-deficient double-bonded carbon. Suitable leaving groups are providing a heteratom (O, N or S) directly attached to the electron-deficient double-bonded carbon of the multiple bond.

An addition reaction involving nucleophilic and electrophilic counterparts can be followed by elimination of water ($H_2O$) if the nucleophilic counterpart comprises $NH_2$-bound to carbon or a heteroatom (e.g. O or N) in combination with an electrophilic counterpart comprising double bonded oxygen. The elimination reaction typically results in an enamine or a ketamine structure ($>C=N-$) which will be particularly favourable when the formed $C=N$ double bond will be part of a conjugated system of multiple bonds and/or links directly to a heteroatom N or S. The corresponding preferences apply for the starting nucleophilic and electrophilic counterparts).

The elimination reaction discussed in the preceding paragraph can be followed by a subsequent cyclization reaction if one of the counterparts comprises an additional nucleophilic group exhibiting a heteroatom X' (O, N, or S) and a hydrogen (H) (nucleophilic group=—X'H). The nucleophilic group (X'H) then should be placed at a distance of 2-3 atoms from XH or from the carbon-oxygen double bond of the electrophilic group for the reaction to proceed smoothly.

Preferred nucleophilic groups are:
a) capable of giving the linkage structure by addition to a counterpart which comprises a keto or aldehyde group possibly followed by elimination of $H_2O$: hydrazide groups e.g. —$CONH_2NH_2$ groups, semicarbazide groups including e.g. semicarbazide —$NHCONH_2NH_2$ groups and carbazate —$OCONH_2NH_2$ groups with preference for the former, thiosemicarbazide groups including e.g. thiosemicarbazide —$NHCSNH_2NH_2$ groups and thiocarbazate —$OCSNH_2NH_2$ groups with preference for the former, aminooxy groups e.g. —$ONH_2$ groups (formation of hydrazone, semicarbazone, thiocarbazone, oxamine linkage structures, respectively),
b) capable of giving the linkage structure by addition to a counterpart which comprises a carbon-carbon multiple bond: thiol groups e.g. —SH (formation of thioether linkage structure),
c) capable of giving the linkage structure by addition to a counterpart which comprises a keto or aldehyde group possibly followed by elimination of $H_2O$ (formation of enamine/ketamine linkage structures) and possibly a second addition (=cyclization): β-aminothiol groups e.g. —$CH(NH_2)CH_2SH$ groups (formation of thiazolidine linkage structures), and
d) miscellaneous: thiocarboxylate anionic groups e.g. —$COS^-$.

Groups according to (a)-(c) are preferred, in particular for in vivo formation of hydrogels since counterparts easily can be selected to give linkage structures of the appropriate stability without releasing anything or only $H_2O$.

Preferred electrophilic groups are:
a) capable of giving the linkage structure by undergoing an addition reaction possibly followed by elimination of $H_2O$ with a counterpart which comprises an $NH_2$— group: aldehyde and keto groups e.g. —CHO groups.
b) capable of giving the linkage structure by undergoing an addition reaction with a counterpart which comprises a thiol group: maleimide groups e.g. $(CHCO)_2N$— groups, acrylate groups e.g. $CH_2=CHCOO$— groups, acrylamide groups e.g. $CH_2=CHCONH$— groups, methacrylate groups e.g. $CH(CH_3)=CHCOO$— groups, methacrylamide groups e.g. $CH(CH_3)=CHCOO$— groups, vinylsulphone groups e.g. $CH_2=CHSO_2$— groups,
c) capable of giving the linkage structure by ring-opening via a substitution reaction with a counterpart comprising a nucleophilic center of the kinds generally discussed above: aziridine groups, epoxide groups, reactive lactone groups and thiolactone groups (electrophilic group/center is part of a ring-structure),
d) capable of giving the linkage structure by a reaction sequence that in total is a substitution with a counterpart that comprises a nucleophilic center of the kinds generally discussed above (include formation of by-products other than $H_2O$): α-halocarbonyl groups e.g. $XCH_2CONH$—, $XCH_2COO$— and $XCH_2CO$— groups in which X is selected amongst halogens, such as Cl, Br and I), thioester groups e.g. —COSR' groups, where R' is lower alkyl such as $C_{1-6}$ alkyl, reactive ester groups e.g. —COOR' groups where R' is alkoxy or aryloxy exhibiting electron-withdrawing substituents, pyridine sulphenyl groups e.g. mercaptopyridyl groups, such as $(C_5H_4N)S$— groups, β-bromoamine groups e.g. $BrCH_2CH(NH_2)$— groups.

Groups according to (a)-(c) are preferred, in particular for in vivo formation of hydrogels. Typical linkage structures for group (a) and (b) are of the same kinds as given for nucleophilic groups (a) and (b), respectively. Typical linkage structures for group (c) are, when the nucleophilic center of the nucleophilic group exhibits an amino nitrogen or an alcoholic hydroxy oxygen, for i) aziridine groups: 1,2-diamino or 1-alkoxy-2-amino, respectively, ii) epoxide groups: 1-amino-2-hydroxy and 2-alkoxy-1-hydroxy, respectively, iii) lactone groups: hydroxy amide and hydroxy ester, respectively, and iv) thiolactone groups: mercapto amide and hydroxy amide, respectively. When thiols are reacting with aziridine groups or oxirane groups, the typical linkage structures will be 1-amino-2-alkylthiooxy or 1-hydroxy-alkylthiooxy, respectively, will be formed. For (iii) and (iv) the hydroxy and the mercapto group will be placed on the acyl moiety of the amide.

The free valence indicated in each group of the preceding paragraphs is binding to a sp-, $sp^2$- or $sp^3$-hybridised carbon which is part of a reactive HA- or a reactive PHP-substituent. A hydrogen H in the parent formulas of the generic groups may be replaced with a group R not negatively affecting the desired reactivity of the parent group. Thus a thiol hydrogen can not be replaced, for instance. A replacement group R is typically inert by not participating in the desired reaction of the parent group and typically is a lower alkyl possibly containing one or more structures selected amongst dialkyl ethers (—O—) or hydroxy. A lower alkyl in this context contains one, two, three, four, five up to ten $sp^3$-hybridised carbons typically with at most one oxygen bound to one and the same carbon.

The reactive HA- and the reactive CLR-group can also be selected amongst reactive counterparts which are capable of participating in cycloaddition reactions. There are two kinds of cycloaddition reactions that are potentially of significant use in the invention
  a) reactions between a diene and a dienophile as counterparts, where the diene comprises at least two conjugated multiple bonds, e.g. two carbon-carbon double bonds, and the dienophile typically exhibits a multiple bond, and
  b) reactions between a multiple bond and a 1-3 dipolar group as counterparts with the basis for the dipole being a chain of three atoms comprising 1-3 heteroatoms selected amongst O, N and S and 0-2 carbons.

Thus in variants of the invention utilizing cycloaddition reactions the pair of counterparts (i.e. the reactive HA-group and the reactive CLR-group) are selected to comprise a first counterpart that comprises a single multiple bond or at least two conjugated multiple bonds, and a second counterpart that comprises a multiple bond or an 1,3-dipolar group as defined in the preceding paragraph. Thus at least one, preferably both, of the two counterparts are selected amongst functional groups that exhibit azide structure, alkyne structure, 1,3-diene structure (e.g. 2-furan structure, 9-anthracenylmethyl structure, hexa-3,5-dien structure, cyclohexane-2,4-dien structure, cyclopentadien structure) and dienophile structure, such as benzoquinone structure.

The Hyaluronan Including its Reactive HA-Substituent

In the present invention the term "native hyaluronic acid" shall refer to an underivatized form of hyaluronic acid irrespective of being a fragment of hyaluronic acid as it exists in nature. The repetitive unit is a disaccharide consisting of D-glucuronic acid and N-acetyl D-glucosamine. Aqueous solutions of native hyaluronic acid are viscous and the viscosity increases with increasing molecular weight and concentration. In principle this also applies to the hyaluronan used in the invention which typical will restrict the use of aqueous liquid formulations containing too high concentrations of hyaluronans and hyaluronans of too high molecular weights.

The hyaluronan in the HA-formulation may be in dry form or in the form of an aqueous liquid in which the hyaluronan is dissolved. The concentration of such solutions may vary within wide ranges. More critical is the actual concentration in the aqueous liquid obtained as a consequence of the activation. Suitable concentrations in this liquid will be determined by desired rigidity, degradation rate, penetratability by a substance in the surrounding medium, ability to release an incorporated therapeutic substance, administratability (related to viscosity) etc and very much will depend on concentrations, substitution degrees, molecular weights, reactivity factors etc of both the hyaluronan and the kind of cross-linking reagent used including also mixability/administratability of the formulations (related to viscosity). Potentially useful concentrations of the hyaluronan in the liquid provided as a consequence of the activation will thus most likely be found in a wide interval, e.g. 0.1-100 mg/mL, such as 1-75 mg/mL. The preferred concentrations are found in the interval of 10-15 mg/mL, such as 12-14 mg/mL.

Suitable sizes/molecular weights of the hyaluronan of the HA-formulation will similar to the concentration depend on desired properties of the final gel which in turn in a complex way is determined by factors similar to those discussed above for the concentration. Potentially useful hyaluronans thus may be found amongst those that correspond to underivatized forms of native hyaluronic acid which have molecular weights in a wide interval, e.g. $0.2 \times 10$-$2 \times 10^3$ kDa, such as $1 \times 10$-$1 \times 10^3$ kDa with preference for $\geq 0.5 \times 10^2$ kDa, and/or $\geq 9 \times 10^2$ kDa, such as $\leq 7 \times 10^2$ kDa or $\leq 5 \times 10^2$ kDa where the term "correspond" means native hyaluronans which have the same number of repetitive units as the hyalurons used in the invention. The preferred range corresponds to native hyaluronic acids in the range of $0.5 \times 10^2$-$5 \times 10^2$ kDa. Corresponding intervals with respect to number of repetitive units/building blocks in hyaluronans are in the interval from 5-5000 repetitive units, such as from 25-2500 repetitive units with preference for $\geq 125$ repetitive units, and/or $\leq 2250$ repetitive units such as $\leq 1750$ repetitive units or $\leq 1250$ repetitive units (based on a Mw of 400 D per disaccharide unit in $Na^+$-form). A preferred range corresponds to 125-1250 repetitive units A reactive HA-substituent is replacing a group which is present in native hyaluronic acid where it is directly attached to the HA-backbone (i.e. to a ring carbon). The substituent may thus be replacing the carboxy or the hydroxy group of a D-glucuronic acid moiety or the hydroxymethyl or the N-acetoamidyl group in an N-acetyl glucosamine moiety of a repetitive unit in hyaluronic acid. An alternative believed to be less preferred comprises that the reactive HA-substituent replaces an aldehyde group obtained by oxidative ring-opening of a glucuronic acid moiety of hyaluronic acid. Based on our own experience and also from what is apparent from the literature, it is believed that derivatization (=replacement) of a native carboxy group to a reactive HA-substituent will result in the most useful hyaluronans.

The hyaluronan of the HA-formulation is devoid of counterparts to the reactive HA-group, i.e. reactive groups that will cause intra-molecular cross-linking of the hyaluronan during the intended cross-linking are in essence missing in the hyaluronan used according to the invention.

A typical reactive HA-substituent provides a spacer between its reactive HA-group and the HA-backbone. The spacer typically comprises one or more bivalent groups selected amongst
  a) amides for instance of carboxylic acids, such as —CXNR$_1$—, —R$_1$NCX—, —OCXNR$_1$—, —R$_1$NCXO—, —R$_2$NCXNR$_1$—, —CXNR$_1$CX— where X is double-bonded oxygen, nitrogen or sulphur,
  b) esters for instance of carboxylic acids —CXO—, —OCX—, —OCXO—, —R$_1$NCO—, and —OCXNR$_1$— where X is double-bonded oxygen, nitrogen or sulphur,
  c) ethers (—X'—, where X' is oxygen or sulphur),
  d) amino (—NR$_1$—), and
  e) straight, branched or cyclic alkylene, e.g. complying with —C$_n$H$_{2n}$— or —C$_n$H$_{2n-2}$—.

R$_1$ and R$_2$ in different bivalent groups of a spacer may be identical or different.

The free valence to the left in each of these bivalent groups is closer to the HA-backbone than the free valence to the right or vice versa. Each free valence is preferably binding directly to an atom carrying the free valence in i) a neighbouring bivalent group of the spacer, ii) a reactive HA-group or iii) the hyaluronan backbone. Oxygen to oxygen bonds shall be avoided. The atom in the bivalent group to which the free valence binds may thus be sp-, sp$^2$-, or sp³-hybridised carbon, or a single bonded heteroatom (—O—, —S—, >N —) or double-bonded nitrogen.

In the alkylene chains according to (e), n is an integer within the interval of 1-10 with preference for 1-5. The alkylene chain may exhibit one or more monovalent groups directly attached to the chain and selected amongst lower alkyl, lower alkoxy, hydroxy lower alkyl, hydroxyl, amino, carboxy etc are bound. Each of these groups may thus replace a hydrogen attached to a carbon of the chain. The carbon chain of (e) may also be interrupted at one or more position by an ether oxygen or an ether sulphur. At most one heteroatom (O, N or S) is preferably bound at one and the same carbon of the bivalent alkylene of (e).

The spacer is preferably hydrophilic by having a ratio between number of heteroatoms O, N, and S and number of carbons that is ≥0.2, such as ≥0.3 or ≥0.4 (hydrophilicity ratio). The spacer is devoid of groups that will act as reactive counterparts to the reactive HA-group of the substituent. These rules for the hydrophilicity ratio are also applicable to other alkyl groups containing heteroatoms discussed in this specification.

A preferred reactive HA-substituent (and also preferred HA-spacers) is replacing a carboxy group of native hyaluronic acid and provides —CONH— directly attached to the HA-backbone via the valence to the left and to the remaining parts of the reactive HA-substituent via the other free valence.

For the same reasons as for concentrations and molecular weights/sizes, useful degrees of substitution (DS) measured (a) as number of reactive HA-substituents per repeating unit (=disaccharide unit) and/or (b) as relative amount of repeating units that carry a reactive HA-substituent may be found in a wide interval, such as ≤80%, such as ≤50% or ≤20%, with preference for ≤15% or ≤10%, with typical lower limits being 0.01% or 0.1% or 1%. A reactive HA-substituent may be dendritic, i.e. exhibiting two or more reactive HA-groups in which case the degree of substitution measured according to (a) may exceed 100%. The preferred reactive HA-substituent is non-dendritic with preferred values of DS found in the range of 1-15%, such as ≤10%.

The Cross-Linking Reagent/Polyhydroxypolymer

The cross-linking reagent in the CLR-formulation may be in dry form or in the form of an aqueous liquid in which the cross-linking reagent is dissolved. The concentration of the solutions may vary within wide ranges. More critical is the actual concentration in the aqueous liquid obtained as a consequence of the activation. Suitable concentrations in this liquid will be determined by desired rigidity, degradation rate, penetratability by a substance in the surrounding medium, ability to release an incorporated therapeutic, administratability (related to viscosity) etc, and very much will depend on concentrations, substitution degrees, molecular weights, and reactivity factors etc of both the hyaluronan and the kind of cross-linking reagent used including also mixability/administratability of the formulations (related to viscousity). Potentially useful concentrations of the cross-linking reagent in the liquid provided as a consequence of the activation will thus most likely be found in a wide interval, such as the interval of 0.1-100 mg/mL or 1-75 mg/mL. The preferred concentrations are found in the interval of 0.5-50 mg/mL, such as 1-10 mg/mL with preference for 1-3 mg/mL for polyvinyl alcohols.

As already has been discussed the cross-linking reagent is a homo-multifunctional cross-linking reagent (CLR-formulation) which
   a) is lacking the backbone of the hyaluronan to be cross-linked (devoid of hyaluronan structure) and
   b) provides a plurality of hydroxyl groups in the cross-linking structure introduced by the reagent.

A preferred cross-linking reagent exhibits one, two, three, four, five or more hydroxy groups. The reagent may or may not exhibit polymeric structure.

The cross-linking reagent is devoid of counterparts to the reactive PHP-groups. In other words reactive groups that will cause intra-molecular cross-linking of the cross-linking reagent during the intended cross-linking are in essence missing in the reagent.

The cross-linking reagents believed to best are found among PHPs which exhibit a PHP-backbone with various kinds of substituents (PHP-substituents) being directly attached to the backbone. Suitable PHPs are biopolymers or are synthetic/artificial polymers.

Typical PHP-substituents are a) reactive PHP-substituents exhibiting a reactive PHP-group, b) hydroxy-containing PHP-substituents, and possibly also c) substituents neither containing a reactive PHP-group or a hydroxy group. The PHP may be a homo- or a copolymer.

Substituents according to (b) and (c) are called inert in the case they are devoid of groups that are counterparts during cross-linking conditions to the reactive PHP-groups of the cross-linking reagent because then they cannot interfere with the desired cross-linking reaction.

A PHP-backbone typically comprises a linear structure of ≥5, or more preferably ≥10 such as ≥25 monomeric units linked together one after the other. Preferably there is no branching of the polymer chain, i.e. preferred PHPs are linear and/or are devoid of cross-links. That a polymer is linear does not exclude that the polymer chain may carry projecting or pending groups of various lengths and kinds as long as such groups are not polymeric and based on the same kind of subunits as the basic chain. A PH-polymer comprises ≥5, with preference for ≥10, such as ≥25 or ≥50 hydroxyl groups and/or ≥5 monomeric subunits each of which exhibits one, two, three, four or more hydroxyl groups per unit.

A backbone of a PHP to be used in the invention thus typically comprises one or more linear structures selected amongst
   a. linear polyamide backbones of identical or different monomeric subunits linked together one after the other with an amide bond (—CONR'₁—,) linking two neighbouring subunits together and with corresponding monomers selected from amino carboxylic acids or combinations of a diamine with a dicarboxylic acid,
   b. linear polyester backbones of identical or different monomeric subunits with an ester bond (—COO—) linking two neighbouring subunits together and with corresponding monomers selected from hydroxy carboxylic acids or combinations of a dialcohol with a dicarboxylic acid,
   c. linear polyether backbones of identical or different monomeric alkylene oxide subunits with an ether bond (—O—) linking two neighbouring subunits together and a straight alkylene chain linking neighbouring ether groups together with the proviso that the chain comprises ≥2 carbons and with corresponding monomers selected from alkylene oxides.
   d. linear polyvinyl backbones of identical or different monomeric C₂-alkylene chain subunits —(CH₂—CH₂—).
   e. polysaccharide backbones that are different from the hyaluronan backbone.

Preferred backbones are believed to be found in group (d) and possibly also in group (e). Backbones of polyvinyl alcohols as used in the experimental part are considered of biggest interest. The most interesting polysaccharide is dextran.

Polymers based on backbones (a)-(c) and (e) may be called condensation polymers since $H_2O$ is formally released during the polymerisation reactions resulting in these polymers.

A group (a) and a group (b) backbone typically comprise a lower alkylene chain linking neighbouring amide groups and neighbouring ester groups, respectively, together. This chain typically is a $C_{1-10}$ alkylene, and is possibly a) interrupted at one or more positions by a heteroatom-containing group, for instance ether oxygen, thioether sulphur, or amino nitrogen, and/or b) substituted with a hydroxy, hydroxy lower alkyl or lower alkyl group, such as $C_{1-10}$. At most one heteroatom (O, N or S) is preferably bound to the same $sp^3$-carbon of the alkylene chain. An important group of polyamides are those that exhibit polypeptide structure, i.e. based on hydroxy-, amino-carboxylic acids as monomers, in particular with the amino group positioned a to the carboxylic group and the hydroxy group being part of an N-hydroxyalkyl or N-hydroxyaryl group, e.g. serine, threonine, tyrosine, proline etc.

The alkylene chains in the subunits of a group (c) backbone may be identical or different between subunits, and are typically selected amongst $C_{2-6}$ alkylenes, such as $C_2$ alkylene or $C_3$ alkylene or combinations of $C_2$ and $C_3$ alkylenes.

In a group (d) backbone a substituent $R^1$ and possibly also a substituent $R^2$ are replacing a hydrogen at the two carbons, respectively [i.e. $-(CHR^1-CHR^2-)$]. At least one of these pending substituents $R^1$ and $R^2$ of ≥50%, such as ≥75% or preferably ≥95%, of the subunits of the backbone exhibits a heteroatom O, N or S while the possibly remaining one of the two pending substituents may by be a lower alkyl, such as ethyl or methyl. At least one of these heteroatom-containing pending $R^1$- and $R^2$-substituents is in preferred variants a hydroxy group or comprises an ester oxygen, an ether oxygen, an amido nitrogen, an amino nitrogen, or a carbonyl carbon such as in keto, amido, and ester, which as indicated in preferred variants are directly attached to one of the two C atoms shown for the $-(CH_2-CH_2-)$ subunit. The preferred group (d) backbone structures comprise the backbone of polyvinyl alcohol $(-[CH_2CH_2(O-)-]_n)$ in which the free valence of the oxygen in ≥50%, such as ≥75% or ≥85%, of the subunits binds to hydrogen or a alkyl or hydroxy alkyl containing one, two or more hydroxy groups. $R^1$ and $R^2$ and may differ between subunits of a polyvinyl backbone. In other polyvinyl backbone structures atoms other than oxygen may be used for linking a pending substituent $R_1$ and $R_2$ to the polyvinyl backbone, e.g. carbon, nitrogen and sulphur.

The reactive PHP-substituent, and, if present, inert hydroxyl-containing PHP-substituents and other PHP-substituents are attached directly to atoms of a selected backbone structure.

Suitable polyhydroxypolymers comprising a polyvinyl backbone (d above) are typically found amongst polymers containing one, two or more different monomeric units deriving from hydroxyalkyl acrylates and methacrylates, N-hydroxyalkyl acryl- and n-hydroxyalkyl methacrylamides, hydroxyalkyl vinyl ethers, vinyl esters etc. Polyvinyl alcohols are typically obtained by partial hydrolysis of polyvinyl esters meaning that polyvinyl alcohols that are preferred in the invention typically exhibit residual amounts of ester groups (≤10% or ≤5%). Hydroxyalkyl comprises alkyl groups in which there are one or more hydroxy groups possibly in combination with one or more ether groups with the proviso that there preferably is at most one oxygen bound to one and the same carbon.

A typical reactive PHP-substituent provides a spacer between its reactive PHP-group and the PHP-backbone. The spacer typically comprises one or more bivalent groups selected amongst the same bivalent groups as those given for a spacer of a reactive HA-substituent.

A preferred reactive PHP-substituent comprises an ester group between the PHP-backbone and the reactive PHP-group. Typical ester functions are selected amongst —OCO—, —OCOO— and —OCONR$_1$— where the left free valence preferably is closer to the PHP-backbone than the right free valence. In preferred hydroxypolymers the left free valence is attached directly to a carbon of the PHP-backbone.

Suitable sizes/molecular weights of the polyhydroxypolymer will similar to the concentration depend on desired properties of the final gel which in turn in a complex way is determined by factors similar to those discussed above for the concentration of the cross-linking reagent Potentially useful polyhydroxypolymers for use in a PHP-formulation may thus be found amongst those in which the number (mean values) of monomeric units are at least 20, 100, 200, 300, 500, 1000, or 2000, and at most 100, 200, 300, 500, 1000, 2000 or 20000 (with a lower limit of an interval always being smaller than the upper limit). Preferred numbers of monomeric units are found in the interval of 200-600 which in particular applies to the polyvinylalcohol used in the experimental part.

For the same reasons as for concentrations and molecular weights, useful degrees of substitution (DS) measured (a) as number of reactive PHP-substituents per repeating unit (=disaccharide unit) and/or (b) as relative amount of repeating units that carry a reactive PHP-substituent may be found in a wide interval, such as ≤80%, such as ≤50% or ≤20%, with preference for ≤15% or ≤10%, with typical lower limits being 0.01% or 0.1% or 1%. A reactive PHP-substituent may be dendritic, i.e. exhibiting two or more reactive PHP-groups in which case the degree of substitution measured according to (a) may exceed 100%. The preferred reactive PHP-substituent is non-dendritic with preferred values of DS found in the range of 1-15%, such as ≤10%.

In the preferred kinds of polyvinylalcohols a repetitive unit can carry at most one reactive PHP-substituent that may carry one or more reactive PHP-group. Examples of potentially suitable PHPs that may carry more than one reactive PHP-substituent per repetitive unit are found amongst polysaccharides, e.g. dextrans and polyvinylalcohols derivatized to exhibit hydroxyalkylether groups in which the hydroxyalkyl groups carries a plurality of hydroxy groups. Other potentially interesting examples are poly(alkyl vinyl ether) polymers in which a plurality of the alkyl groups carries a plurality of hydroxy groups and possibly with the carbon chain of the alkyl group being interrupted at one or more positions by an ether bond with the proviso that preferably at most one oxygen is bound at one and the same $sp^3$-hybridised carbon.

Other Features of the Formulations of the Compositions and Vehicles for the Composition.

The composition of the invention typically comprises a buffer system that shall provide a physiologically acceptable pH in the aqueous liquid in which the cross-linking reaction and hydrogel formation are to take place. Physiological acceptable in this context means acceptable for the individual to whom the composition is to be administered and includes pH values that are outside what is normally contemplated for healthy individuals. Thus suitable pH-values for the invention are found within the pH-range of 4.5-9, with preference for 5.5-8.5. These ranges typically apply for the above-mentioned aqueous liquid and possibly also for one or more of the formulations given above, e.g. the HA- and/or the CLR-formulation. Buffering components of the buffer system selected may be present either in one or both of the HA- and CLR-formulations and/or in a separate buffer formulation. The buffering components may differ between the formulations of a composition both with respect to kinds and relative amounts. It follows that the pH-value provided by buffering components in one of the formulations may be different from the pH-value provided by the buffering components in the other formulation. The pH-value may be physiologically unacceptable in one or both of the HA- and the CLR-formulation as long as mixing of the two formulations with each other possibly supplemented with buffer components from a separate buffer formulation will result in physiologically acceptable pH conditions in the final aqueous solution after activation is completed. Physiologically unacceptable pH-conditions may be appropriate and even advantageous in a single formulation, among others for stability reasons of particular variants and combinations of reactive counterparts, for instance.

The composition may also contain various kinds of salts to properly provide acceptable ionic strengths and the like in the aqueous solution in which cross-linking and hydrogel formation are to take place. Such salts may be present in either one or both of the HA- and CLR-formulations and/or in a separate formulation, for instance.

One, two or more of the different formulations of the composition may be in aqueous liquid form or in solid form, e.g. a solid form which is possible to reconstitute to aqueous liquid form. Solid forms comprise powder forms, dehydrated forms such as lyophilized forms, spray-dried forms, air dried forms, etc with reconstitution to aqueous liquid form (solution) typically taking place during the activation of the composition.

The composition may also comprise a compartmentalized vehicle in which there for each formulation of the composition typically is a separate compartment with an outlet conduit that ends in an outlet of the vehicle. The outlet of the vehicle may be common or separate for two or more compartments which in particular applies to the compartments for the HA- and the CLR-formulations. The outlet of these preferred vehicles shall thus be
  a) common for the formulations, in particular the HA- and the CLR-formulations thereby allowing administration of a mixture of the formulations, i.e. an activated form of the composition (in aqueous liquid form) as required by the intended use and discussed elsewhere in this specification, or
  b) separate for the formulations permitting parallel administration of the formulations with the final step in the activation (mixing) taking place at the location to which they have been administered.

These kinds of vehicles are preferably in the form of a compartmentalized syringe of the kind well-known in the field and used in the experimental part. The compartments of the vehicle may be replaceable permitting compartments of different volumes facilitating the use different relative amounts of the formulations of the composition, for instance the HA- and CLR-formulations.

Other vehicles are also possible, for instance separate vessels (ampoules, bottles etc) for the different formulations. These vessels may be storage vessels from which aliquots are transferred to the corresponding compartments of a compartmentalized vehicle.

The HA- and the CLR-formulation of the inventive composition are typically delivered to the customer or end user either separately or together. There are typically attached a package insert and/or a manual of use referring to the HA- and the CLR-formulation and/or a use as discussed elsewhere in this specification.

The composition of the invention may also contain one or more formulations containing a population of particles (particle formulations). The particles may or may not be bioactive. A particle formulation may coincide with one or more of the formulations discussed above or is a separate formulation, with preference for either one or both of the HA- and CLR-formulations also being a particle formulation. The particles should at least be dispersible in the aqueous liquid which contains both the hyaluronan and the cross-linking reagent and is obtained as a consequence of activation of the composition.

A particle formulation may be devoid of aqueous liquid with the particles being present as a dispersible powder or a dehydrated form, e.g. of the kinds discussed above for other formulations. The preferred particle formulations are similar to the preferred HA- and CLR-formulations in the sense that both of them are based on the presence of an aqueous liquid. The particles are during storage of the formulation maintained in dispersed form or alternatively settled but dispersible.

Dispersible particles populations are typically nanosized (nanoparticulate), i.e. have a mean size in the nm-range, i.e. ≤5000 nm, such as ≤1000 nm with typical lower limits being 0.1 or 0.5 nm.

Particles of the composition may act as a filler agent for the hydrogel to be formed and will then typically improve the mechanical strength of the gel. Filler particles may be based on organic material and/or inorganic material. Suitable inorganic material is typically biocompatible, such as apatite, titanium etc.

The particles may be bioactive, e.g. be a therapeutically active. In most instances bioactive particles may also act as filler agents.

Typical useful bioactive particles with characteristics as outlined above may contain
  a) bioactive inorganic material, e.g. $Ca^{2+}$ in salt form with phosphate as counter-ion for instance, such as dispersible nanoparticulate forms of apatite and other variants of calcium phosphate, and/or
  ii) bioactive organic material, e.g. of bioorganic origin such as immunogenic bio-organic material deriving from unicellular organisms, such as bacteria, fungi etc, viruses, plants and animals
  iii) organic and/or inorganic material to which a bioactive substance of the kinds discussed below is immobilized.

The composition of the invention may also contain a bioactive substance that is not in particle form but in soluble/dissolved form. The most important such substances are therapeutically active compounds such as drugs. They typically exhibit at least one structure selected amongst peptide structures (including polypeptide structures (such as oligopeptide structures) and protein structures), nucleotide structures (including i.a. polynucleotide structures), carbohydrate structures, steroid structures, lipid structures, antioxidant structures, vitamin structures etc and structures of drugs in the form of low molecular weight organic compounds of molecular weights<5 kDa, such as <2 kDa or <1 kDa with a typical lower limit of 0.1 kDa.

The bioactive substance may be free to dissociate from the hydrogel without need for breaking a covalent bond between the substance and the cross-linked network of the hydrogel. This does not exclude that there may be variants in which the bioactive substance is covalently attached to the hydrogel and not released until a covalent bond immobilizing the substance to the hydrogel is broken.

In certain other variants the bioactive substance may be present in the HA-formulation or in the PHP-formulation covalently immobilized or covalently immobilizable to the hyaluronan or the PHP. If the bioactive substance is immobilizable, immobilization can take place prior to, during and/or subsequent to hydrogel formation, e.g. by reacting with excessive amounts of a counterpart group. In most of these variants the major route for release of the substance is by degradation in vivo of the hydrogel.

Growth factors are typical bioactive substances which exhibit peptide structure. A growth factor typically has a relatively high molecular weight, such as ≥2 kDa, such as ≥5 kDa or ≥10 kDa, induces proliferation and/or differentiation of cells, and/or preferably is active locally when present in vivo. Typical examples are growth factors of the TGF-family including osteoinductive growth factors such as various bone morphogenetic proteins, for instance BMP-2, -4, -6, -7, -12, and other growth factors such as vascular endothelium growth factors (VEGF), epidermal growth factors (EGF), fibroblast growth factors (FGF), nerve growth factors (NGF), platelet derived growth factor (PDGF), insulin-like growth factors, such as IGF-1.

Important tissue generation applications of hydrogels prepared from the compositions of the invention are:
i) Hydrogels containing osteoinductive growth factors may be used to improve fracture healing or heal bone defects including spinal fusion procedures. The use for enhanced osseointegration of implants, such as dental and orthopaedic implants, is also included
ii) Hydrogels with a particle additive, such as hydroxyapatite and/or tricalcium phosphate, may enhance the amount of bone formation. The hydrogel with particle additives may function without osteoinductive BMPs as bone conductive agent for the healing of bone fractures, bone defects, and improved osseointegration of bone implants. Hydrogels containing a particle additive, and osteoinductive BMPs are likely to allow osteoconduction and/or osteoinduction.
iii) Hydrogels containing particle additives and with or without osteoinductive growth factors, may not only be beneficial in the treatment of bone defects but also in generalized bone disease including osteoporosis. This kind of composition may be injected into bones.
iv) Hydrogels with or without hydroxyapatite particles, containing members in the BMP-family of growth factors, including BMP-2, -4, -6, -7, -12, -13, and growth and differentiation factor-5 (GDF-5) may be therapeutically beneficial for healing of localized or generalized cartilage defects and tendon repair.
v) Hydrogels containing purified or recombinant growth factors including VEGF, EGF, FGF, NGF, PDGF, IGF-1 etc may be used for local administration for obtaining a local cellular response and tissue regeneration including vascular formation and dermal/epidermal healing.

Chemotherapeutics drugs (bioactive substances) of the type discussed above may be incorporated in the composition and be beneficial in cancer treatment by local and/or systemic sustained release of the drug.

A bioactive substance of the type discussed above, e.g. a bioactive peptide (typically of oligopeptide structure), may be incorporated in an inventive composition intended for local or systemic in vivo administration and response.

A bioactive substance/drug of the type discussed above, for instance an antagonist such as a TNF-alpha antagonist, may be incorporated in an inventive composition intended for sustained release and therapeutic effects of the bioactive substance in vivo.

A bioactive substance of the type discussed above, such as a drug which may be a hormone or a steroid, e.g. a growth hormone, insulin, corticosteroid etc, may be incorporated in an inventive composition intended for delivery and slow release in vivo for achieving a therapeutic effect.

An immunogen may be incorporated in an inventive composition intended to be used as a vaccine adjuvant for immunization in order to accomplish antibody/humoral and cell-mediated immune responses.

Nucleic acids such as cDNA or siRNA may be incorporated in an inventive composition intended for research and/or therapeutic purposes.

A vitamin may be incorporated in an inventive composition intended to be used for administration of vitamins by injection. The vitamin-depot may allow systemic release of antioxidants (vitamin C and E) and/or specifically target immune cells for instance lymphocytes leading to improved anti-viral, anti-bacterial, and/or anti-cancer effects mediated by the immune system.

A second main aspect of the invention is the composition of the first aspect for use in vivo or ex vivo as a support matrix. This kind of uses encompasses applications in vivo using the support matrix (=the hydrogel formed) in tissue generation including both tissue generation and tissue engineering, as a sustain release storage for a bioactive substance of the kinds discussed above (e.g. a therapeutics, an immunogen etc), in cosmetic surgery (breast implants, tissue augmentation/anti-wrinkling etc), in keeping tissue together (tissue gluing), in keeping tissue apart (tissue separator), for promoting the presentation of a bioactive substance to receptors in vivo (e.g. as an adjuvant as discussed above) etc.

The use aspect also comprises the use of a HA-formulation and a CLR-formulation of the kinds discussed above for the manufacture of a composition of the first aspect to be used for the treatment of an individual considered to be in need for the support matrix obtained by activation of the composition and formation of the corresponding hydrogel in vivo at the desired location within the individual.

A third main aspect of the invention is a method for providing in vivo a support matrix for one or more of the purposes discussed above to an individual or an organ deemed to be in need for the support matrix for these purposes. The method comprises the steps of:
i) providing a composition as discussed for the first aspect, preferably with said formulations being in aqueous liquid form,
ii) activating said composition to give a common aqueous liquid containing said hyaluronan and said cross-linking reagent, and, if present in the composition provided in step (i), said buffer, said particles and/or said bioactive substance,
iii) administering the liquid obtained in step (ii) to the location within said individual or said organ so that a hydrogel will be formed at said location containing, if present in the composition provided in step (i), said particles and/or said bioactive substance.

The method may comprise optional steps. One such step may be a fourth step comprising administering a bioactive substance to the gel formed in vivo during step (iii) if said individual or said organ is deemed in need for this substance. This step in particular applies if a desired bioactive substance was not including in the composition provided in step (i) or if an additional dose is needed of a substance included from the beginning.

BEST MODE

The embodiments that are believed to be best are illustrated in Part A of the experimental part with believed preferences as outlined in other parts of the specification.

EXPERIMENTAL PART

A. In Vivo Study and Characteristics of the Material Used
Synthesis of Polymers and of Gels
Synthesis of Hydrazide-Modified Polyvinyl-Alcohol (PVAH).

PVA with 5% hydrazide functionality was prepared and characterized as described previously (Ossipov et al *J. Appl. Polym. Sci.* 2007 106 60-70). The molecular weight ($M_w$) of the starting PVA was 16 kDa.

Synthesis of Aldehyde-Modified Hyaluronic Acid (HAA).

Aminoacetaldehyde dimethyl acetal modified hyaluronic acid was prepared by following a previously described protocol (Bergman et al *Biomacromolecules* 2007 8 2190-2195), and was further hydrolyzed to obtain the aldehyde derivative. In detail, hyaluronic acid sodium salt from *Streptococcus equi* ($1.5 \cdot 10^6$ Da, Fluka) was dissolved in deionized water (5 mg/mL, pH 6.85) and mixed with Dowex $H^+$. The mixture was shaken at r.t. for 1 h, filtered and the solution (pH 2.85) freeze-dried to obtain hyaluronic acid in protonated form. HA (1.52 g, 4 mmol carboxylic acid) was dissolved in 60 mL deionized water in a 250-mL round-bottomed flask followed by the careful addition of 40 mL acetonitrile while stirring. To the solution was added 0.45 mL 4-methylmorpholine (4 mmol), which raised pH to 7. The solution was cooled to 4° C., 281 mg 2-chloro-4,6-dimethoxy-1,3,5-triazine (1.6 mmol) was added and stirred with a magnetic stirrer for 10 min at r.t. The solution was mixed with 0.44 mL aminoacetaldehyde dimethylacetal (4 mmol) and stirred for another 20 h. Dowex H+(4 mL) was then added to the reaction mixture, the magnetic stir-bar removed, the flask agitated for 15 minutes and the solution filtered. This procedure was repeated using 10 mL Dowex saturated with sodium and the solution was concentrated by evaporation, dialyzed exhaustively (1000 MWCO) and lyophilized to give 1.42 g hyaluronic acid modified with 16% aminoacetaldehyde dimethylacetal (as determined by $^1$H NMR spectroscopy). The product was dissolved to a concentration of 10 mg/mL in 0.5 M HCl and stirred for 3 h before neutralizing with 4 M NaOH. Dialysis and lyophilization yielded 1.3 g aldehyde-modified HA (HAA).

Determination of Substitution Degree of HAA.

The average number of aldehyde groups per repeat unit of HAA was determined by an aldehyde assay (Jia et al *Macromolecules* 2004 37 3239-3248). Briefly, two 5-mL solutions of acetate buffer (pH 5.2) were prepared, one containing 50 mg HAA, and one containing 83 mg t-butyl-carbazate and 40 mg sodium cyanoborohydride. A mixture of the solutions was stirred at r.t. overnight and dialyzed against 0.1 M NaCl for 20 h and against deionized water for 24 h. The solution was freeze-dried and the residue (45 mg) characterized by $^1$H NMR spectroscopy (JEOL ECP 400 MHz spectrometer) in $D_2O$ at 80° C. The substitution degree of 5% was determined by comparing integrals of the methyl signal at 1.94 ppm (3H) with the t-butyl signal at 1.4 ppm (9H). Molecular weight determination of HAA. The molecular weight of HAA of 90 kDa was determined by performing static light scattering measurements as described previously (Bergman et al *Biomacromolecules* 2007 8 2190-2195).

Presentation and Characterization of HAAPVAH-Gels
Preparation of HAAPVAH-Gels.

HAA was dissolved in PBS (pH 7.4, Biochrom AG) to a concentration of 26.7 mg/mL (3.3 mM aldehyde). PVAH was dissolved to a concentration of 3.3 mg/mL (3.3 mM hydrazide) in 0.3 mg/mL rhBMP-2 solution (InductOS®, Wyeth Europe Ltd.) for gels containing BMP-2. The BMP-2 solution was prepared by adding deionized water to a lyophilized powder of the protein in a formulation buffer of pH 4.5 containing glycine, sucrose, polysorbate 80, sodium chloride and L-glutamic acid. The concentration of BMP-2 in the solution was confirmed by performing a Quantakine Colorimetric sandwich ELISA assay (R&D Systems Europe Ltd.). PVAH was dissolved to the same concentration in the formulation buffer alone for gels w/o BMP-2. HAA and PVAH solutions were filtered through sterile 0.45 µm syringe filters and HAAPVAH-gels were formed by mixing equal volumes of each solution using two 1-mL syringes, a Duploject™ syringe device (Baxter) and 21-gauge needles.

Gelation Time.

The gelation time for HAAPVAH-gels was determined by injecting 0.7 mL of each polymer solution by the use of a dual barrel syringe into a glass tube (0.8×7.4 cm) placed in a water bath at 37° C. The total polymer concentration was 1.5%. The tube was tilted 90-180° C. every 5 s and the gelation time was defined as the time when the sample did not flow. The experiment was performed in triplicate. The found gelation time was 38±6 s.

Swelling.

Gels discs with 20 mm in diameter were prepared by injecting 0.7 mL each of HAA and PVAH into cylindrical PTFE moulds that were covered with a glass slide to avoid evaporation. After 24 h the initial weight ($W_i$) was measured and the gels were transferred to 50-mL tubes filled with PBS. The tubes were incubated at 37° C. for 96 h and the swollen weight of the gels ($W_s$) was measured after removing the gels and gently blotting with a paper tissue. The additional amount of absorbed PBS was determined by $(W_s-W_i)/W_i$. The experiment was performed in triplicate. The gels increased their weight 24±6% by swelling.

Rheology.

An AR2000 Advanced Rheometer (TA Instruments) was used to determine the shear storage modulus, G', of 1.4-mL gel-discs prepared in cylindrical PTFE moulds with 20 mm diameter. The gels were allowed to settle for 24 h and were incubated in excess PBS at 37° C. for 3 days. Gels were gently blotted with a paper tissue before performing an oscillatory stress sweep at 37° C. using a titanium plate geometry with 19 mm in diameter. G' was measured as a function of shear stress, from 10 Pa to 100 Pa, at an oscillating frequency of 1 Hz and with an applied normal force of 0.6 N. The storage modulus presented is an average value over the stress range from three measurements. An elastic modulus (G') of 728±36 Pa was determined for the gel.

Preparation of Gels Containing Hydroxyapatite Particles.

HAAPVAH-gels (w. or w/o. rhBMP-2) were also prepared containing hydroxyapatite powder (Plasma Biotal Ltd.). The hydroxyapatite-particle powder (HAP) was placed in a glass vial sealed with aluminum foil which was sterilized by heating to 200° C. for a minimum of 1 h. The polymer solutions were prepared as above and were each mixed with 25% (weight to volume) of the powder to form a suspension. Gels were then formed by injection using a dual-barreled syringe as described above.

Cell Viability

Human dermal fibroblasts (hDFn) were cultured in complete DME/F12 medium (Dulbecco's Modified Eagle's Medium/Nutrient Mixture F-12 Ham with L-glutamine, 15 mM HEPES and sodium bicarbonate (DME/F12) supplemented with 10% fetal bovine serum). Cells were maintained at 37° C., 5% $CO_2$ and used at passage 7. Gels (0.2 mL), with and w/o HAP) were each prepared in triplicate in 5-mL tubes as described above. Each gel was allowed to settle for 1 h and was then covered with 4 mL of complete DME/F12 medium with 10% FBS and incubated at 37° C. for 1 week. Human dermal fibroblasts (hDFn) were seeded in 96-well plates at a density of 2.5×104 cells/mL (200 µl/well) and cultured in complete DME/F12 medium at 37° C., 5% $CO_2$ for 24 h. The old medium was removed and 200 µl of the medium incubated with gels was added to each well (6 wells/gel). The plates were incubated at 37° C., 5% $CO_2$. Complete DME/F12 medium without material was incubated at 37° C. for 1 week and used to culture cells as a negative control. After 0 h, 24 h and 48 h cell viability was determined through a colorimetric MTT assay. At each time point 20 µl of sterile 5 mg/mL MTT solution (Thiazolyl Blue Tetrazolium Bromide in PBS) was added to each well and the plates were incubated at 37° C., 5% $CO_2$ for 3.5 h. Thereafter the medium was carefully removed and the blue crystals dissolved in 200 µl DMSO. After a few minutes absorbance was measured at 570 nm. The cytotoxicity of gels was assessed from the relative cell viability results. No apparent cytotoxic effect could be detected. The results are presented in the table below

TABLE 1

Cell viability. The values show the relative absorbance from the MTT assay for cells grown in the presence of medium that was incubated with the gels for 1 week.

| Time (h) | Relative absorbance at 570 nm (%) | |
|---|---|---|
| | HAAPVAH gels | HAAPVAH gels with HAP |
| 0 | 99 ± 7 | 109 ± 13 |
| 24 | 90 ± 10 | 96 ± 9 |
| 48 | 95 ± 6 | 81 ± 7 |

In Vitro Release Kinetics.

Gels (0.35 mL, 52.5 µg rhBMP-2) formed in 5-mL tubes were allowed to settle for 1 h at r.t. before adding 4 mL PBS and incubating the samples at 37° C. At different time-points the release medium was removed, stored at −20° C. and replaced with fresh PBS. After 28 days the gels were degraded by replacing the removed release medium with 1 mL bovine testicular hyaluronidase of 1000 U/mL in citrate buffer (pH 5.5). The amount of BMP-2 in collected release medium and degraded gels was then determined by performing a Quantakine Colorimetric Sandwich ELISA assay (R&D Systems Europe Ltd.). The experiment was performed in triplicate.

Results.

A cumulative release profile suggests that 8% of the loaded BMP-2 was released during the first 5 days and only 12.5% in total, including the amount recovered after degradation (≤1%). The nucleophilicity of the hydrazide groups on the PVA derivative are stronger than that of any groups on the BMP-2 molecule, and should thus react selectively with the aldehyde groups on the hyaluronan derivative excluding the risk of forming a hyaluronan/BMP-2 conjugate. Nonetheless we chose to include BMP-2 with the PVA-component since unwanted reactions with the aldehyde might occur in the absence of stronger nucleophiles. Perhaps a more plausible explanation to the low amount of released BMP-2 is that a significant amount of the protein is lost due to its instability at the elevated temperature (Schwartz et al Eur. J. Pharm. Bioparm 2006 63 241-248). It cannot, however, be ruled out that BMP-2 interacts with components in the gel or is affected by the surrounding environment to become unrecognized by the detection method used, and yet maintain its activity.

Implantation in Rats

Animal procedures were approved by the local ethical committee at Karolinska Institute (N70/05). Induction of ectopic bone formation were studied in anesthetized (Isofuran, Abbott Scandinavia, Sweden) adolescent male Sprague Dawley rats (n=20) weighing 250-300 grams. HAAPVAH gels (0.2 mL, with or w/o rhBMP-2, with or w/o HAP) were injected into quadriceps muscles using both legs. The animals were allowed to move freely after the procedure and were euthanatized by $CO_2$ after 4 or 10 weeks. Dissected legs were preserved in 4% paraformaldehyde and examined by radiography. Samples examined by histology were further decalcified (Stephens Scientific, N.J.) and cut into 5-µm paraffin sections which were stained with Trichrome-Mason. Clear skeletal preparation was performed by boiling samples in water for 3 h and treating with 10% $H_2O_2$.

Results.

Radiographic examinations 4 weeks after implantation of gels containing BMP-2 but no HAP showed the formation of ectopic bone at the site where gels were injected. Ectopic bone samples (from 4 weeks) were also cleared from surrounding tissue by boiling in water in order to obtain a three dimensional view of their morphology, which appears to be characterized by the geometry of the injected gel. Ectopic bone formation at the site of injection, including mineralized tissue surrounding a bone marrow cavity, was demonstrated by histology. Arteries and veins were found in adjacent soft tissues in BMP-2-hydrogel specimens, but not in the controls indicating the concurrent induction of vascular tissue by BMP-2. Interestingly, the infiltration of inflammatory cells, including giant cells and lymphocytes, was completely absent in the BMP-2-hydrogel group and in the control. No sign of hydrogel was seen after 4 weeks in the control group indicating complete degradation within this time.

Radiographic examinations 4 and 10 weeks after implantation of gels containing HAP with or without BMP-2 show the formation of ectopic bone at the site of injection of the gels with BMP-2 and HAP. The newly formed bone was more radiopaque indicating the formation of ectopic bone with a higher density as compared to bone induced by gels with BMP-2 but without HAP. The control, gel with HAP but without BMP-2, was not radiopaque in itself. The higher bone density was further demonstrated by histology after 4 and 10 weeks post-implantation. Surprisingly, in addition to ectopic bone formation cartilage and tendon-like structures were present at the injection site and was persistent after 10 weeks histologically. The diverse tissue response with bone, cartilage and tendon-like tissues induced by the gel with BMP-2 and HAP demonstrate the formation of enthesis, a structural region at which a tendon inserts into bone. The tendon-like structures was also demonstrated macroscopically. Here, the ectopic bone seemed to be connected to the adjacent bone/tendon structures of the rat. No inflammatory reaction was seen at the implantation site.

Subcutaneous Injections in Rats:

To assess degradation rate of the hydrogel without additives 0.5 mL was injected subcutaneously into adolescent male Sprague Dawley rats weighing 250-300 grams (n=6).

The rats were anesthetized by Isofuran, (Abbott Scandinavia, Sweden) and subcutaneous injections were performed at the back of the rats. The animals were allowed to move freely after the procedure and were euthanatized by $CO_2$ after 5 or 8 weeks. Dissected samples were preserved in 4% paraformaldehyde and examined by histology. Preserved samples were cut into 5-μm paraffin sections and stained with Hematoxillin-Eosin.

Results:

At the 5-week time-point the subcutaneously implanted gels were almost completely degraded and only small residues in three animals could be detected and harvested for further analysis. At the 8-week time-point no residual gels were found in any animal. Histological examinations from the 5-week group revealed hydrogel without infiltrative cells and normal adjacent tissue including fat and muscle.

Treatment of Large Animal Bone Defects

The hydrogel with hydroxyapatite particles (here referred as hydrogel) was tested as BMP-2 delivery vehicle for the repair of critical sized cranial defects in minipigs. A cranial defect measuring 2×4 cm was created and the defects was filled with 5 mL hydrogel alone (N=6) or with 5 mL hydrogel with 1.25 mg rh BMP-2 (0.25 mg BMP-2/mL hydrogel, N=6). Sham operated pigs, with untreated cranial defects, were controls (N=2). 12 weeks after surgery the animals were euthanized. Necropsy of the inner organs including brain, heart, liver, kidney and bowels showed no pathological changes. High resolution CT scans 12 weeks after surgery revealed complete and massive regeneration of the bone in the defect in all animals treated with hydrogel with BMP-2. In the group treated with hydrogel alone, without growth factors, island-like bone formations were observed but the amounts of newly formed bone was statistically less as compared to hydrogel+BMP-2 (p=0.028). In the sham operated control group large bony defects still remained, filled with connective tissue and fluid. The density of newly formed bone was measured from CT-scans in Hounsfield units, with no statistically significant difference seen between the groups. The histological examination of all three groups showed healthy bone with active osteoblasts lining bone lacunas, occasional osteoclasts facing the dura mater. The bone in the group treated with hydrogel+BMP-2 was generally more mature with increased mineralization and more lamellar growth as compared to defects treated with hydrogel alone. In the sham operated control group the bone was of the same quality as in the hydrogel group but in smaller amounts and with larger proportions of connective tissue.

Treatment of Small Animal Bone Defects

The healing of critical sized bone defects was assessed in rats. A femoral defect measuring 8 mm was created on each animal and treated with 0.2 mL hydrogel with hydroxyapatite particles (here referred as hydrogel) with 1 μg BMP-2 (conc. 5 μg BMP-2/mL hydrogel), 0.2 mL hydrogel with 25 μg BMP-2 (conc. 125 μg BMP-2/mL hydrogel), 0.2 mL hydrogel alone or sham operated control with untreated defects. The treated femoral bones were stabilized by external fixation. Bone formation and healing were assessed by radiography at 2½ and 5 week time-points.

A complete healing was seen in the groups treated with hydrogel+1 μg BMP-2 and hydrogel+30 μg BMP-2 already after 2½ weeks. Excess amounts of newly formed bone was seen in the latter group demonstrating the effectiveness of the hydrogel as delivery vehicle for BMP-2 and the need to down-regulate BMP-2 amounts using this compound. Incomplete healing of the defects was seen in the hydrogel and control groups after 12 weeks.

Reduction Of Scar Formation

The use of the hydrogel at the time of surgery may be beneficial for the reduction of scar formation in tissues, including skin. Here, the hydrogel is injected at the incision site and allowed to form a gel in situ prior to surgery. The hydrogel can potentially inhibit migration of resident fibroblasts into the wound and instead allow mesenchymal cells to invade and induce scarless healing. The hydrogel may be used alone or together with a growth factor, such as TGF-beta-3 or platelet derived growth factor, for this indication.

B. Synthesis of Polyvinyl Alcohol (PVA) and Hyaluronic Acid Derivatives and Their Characteristics (PVAs)

The structure of synthesized polymer derivatives were confirmed by NMR carried out on Jeol JNM-ECP Series FT NMR System at a magnetic field strength of 9.4 T, operating at 400 MHz for $^1H$.

Synthesis of thiolated PVA 1.

PVA (200 mg, 0.0125 mmol, 4.5 mmol of OH-groups) was dissolved in dry DMSO (4 mL) under heating and the solution was dried by addition of some amount of dry toluene followed by its azeotropic distillation using a Dean Stark trap before starting the reaction. CDI (365 mg, 2.25 mmol) was added in one portion to the magnetically stirred PVA solution under argon atmosphere at room temperature. The reaction mixture was then stirred under argon at room temperature for another 2.5 h. 2-(2-pyridyldithio)ethylamine hydrochloride (Ebright et al *Biochemistry* 1992 31 10664-10670) (100.2 mg, 0.45 mmol) followed by triethylamine (63 μL, 0.45 mmol) were added to the reaction solution. Stirring was continued at room temperature and argon atmosphere overnight. Afterward 2 mL of concentrated aqueous $NH_3$ was added and the mixture was stirred for 45 min at room temperature. Finally, the reaction mixture was diluted with 10 mL water, filtered until clear, and reduced to ~4 mL volume by rotary evaporation. The residual gel material swollen in DMSO was treated with DTT (694 mg, 4.5 mmol) under exclusion of oxygen which led to gel degradation within 10 min. Clear DMSO solution was stirred with DTT under argon for 48 h more. The solution was diluted with dilute HCl (pH 3) and transferred to 1000 $M_w$ cut off dialysis tubing. Dialysis was performed twice against dilute HCl (pH 3). The dialyzed solution was subsequently freeze-dried to give white solid product, 4.5%-PVA-$(OCONHCH_2CH_2SH)_n$. DS 0.045. MW~17670.

Synthesis of Cysteine-Modified PVA 3.

PVA (200 mg, 0.0125 mmol, 4.5 mmol of OH-groups) was dissolved in dry DMSO (4 mL) under heating and the solution was dried as described before. CDI (365 mg, 2.25 mmol) was added in one portion to the magnetically stirred PVA solution under argon atmosphere at room temperature. The reaction mixture was then stirred under argon at room temperature for another 2.5 h. N-Boc-S-trityl-N-2-amino-ethyl-L-cysteinamide (Wood et al *Bioconjugate Chem.* 2004 15 366-372) (227.5 mg, 0.45 mmol) was added to the reaction solution and the resulting mixture was stirred overnight at room temperature. Afterward 2 mL of concentrated aqueous $NH_3$ was added and the mixture was stirred for 45 min at room temperature. Finally, the reaction mixture was diluted with 10 mL water, stirred for 1.5 h more, and reduced to ~4 mL volume by rotary evaporation. The residual DMSO solution that contained the product with protected amino and thiol groups was precipitated by addition of 50 mL of water. The precipitate was filtered off and treated with TFA (4 mL) for 30 min which led to complete solubilization of the material. TFA was then evaporated and the residue was triturated with diethyl ether to give the intermediate PVA derivative 2, 5.1%-PVA- (OCONHCH$_2$CH$_2$NHCOCH(NH$_2$)CH$_2$STr)$_n$, as a white solid. DS 0.051. MW~23750.

The solid PVA 2 (222 mg, 0.0094 mmol, 0.173 mmol of STr-groups) was dissolved in TFA/water (5 mL, 4:1) and dichloromethane (1 mL) followed by triisopropylsilane (75 µL) were added to the solution. The two-phase mixture was stirred vigorously for 15 min at room temperature. The mixture was then evaporated, co-evaporated with water, re-dissolved in 30 mL of water again, and the insoluble material was filtered off. The filtrate was dialyzed against dilute HCl (pH 3.0) two times. The dialyzed solution was subsequently freeze-dried to give the white solid product, 5.1%-PVA-(OCONHCH$_2$CH$_2$NHCOCH(NH$_2$)CH$_2$SH)$_n$, 3. DS 0.051. MW~19450.

Synthesis of Aminooxy-Modified PVA 4.

PVA (207 mg, 4.66 mmol of hydroxyl groups) was dissolved in dry DMSO (4 mL) and the solution was dried as described before. CDI (378 mg, 2.33 mmol) was added in one portion to the magnetically stirred PVA solution under argon atmosphere at room temperature. The reaction mixture was then stirred for another 2.5 h. tert-Butyl 3-aminopropoxycarbamate (Salisbury et al *J. Am. Chem. Soc.* 2002 124 14868-14870) (89 mg, 0.46 mmol) in 2 mL of DMSO was added to the reaction solution and the resulting mixture was stirred overnight at room temperature. Afterward 2 mL of concentrated aqueous NH$_3$ was added and the mixture was stirred for 45 min at room temperature. Finally, the reaction mixture was diluted with 25 mL water, stirred for 2 h more, and reduced to ~6 mL volume by rotary evaporation. The substituted polymer was precipitated from the residual DMSO solution by adding 10-fold excess of an 80/20 (v/v) mixture of diethyl ether/ethanol. The precipitated polymer was then directly deprotected by treatment with TFA/water (8 mL, 95:5) for 1 h at room temperature. The reaction solution was evaporated to dryness and 20 mL of water was added to the remaining residue. The pH was adjusted to 10 which caused complete solubilization of the material (it was poorly soluble at acidic pH). The solution was filtered and the filtrate was dialyzed 1000 M$_w$ cut off tubing against water two times, and finally freeze-dried to give 4.6%-PVA-(OCONHCH$_2$CH$_2$CH$_2$ONH$_2$)$_n$, 4. DS 0.046. MW~17920.

Synthesis of Amino-Modified PVA 6.

PVA (800 mg, 0.05 mmol, 18 mmol of OH-groups) was dissolved in dry DMSO (16 mL) under heating and the solution was dried as described before. CDI (1.56 g, 9 mmol) was added in one portion to the magnetically stirred PVA solution under argon atmosphere at room temperature. The reaction mixture was then stirred under argon at room temperature for another 2.5 h. (N-tert-butyloxycarbonyl)ethylenediamine (Xu et al *Synthesis* 2003, 8, 1171-1176) (177.6 mg, 1.11 mmol) in 6 mL of DMSO was added to the reaction solution and the resulting mixture was stirred overnight at room temperature. Afterward 8 mL of concentrated aqueous NH$_3$ was added and the mixture was stirred for 45 min at room temperature. Finally, the reaction mixture was diluted with 50 mL water, stirred for 2 h more, and reduced to ~16 mL volume by rotary evaporation. The substituted polymer was precipitated from the residual DMSO solution by adding 10-fold excess of an 80/20 (v/v) mixture of diethyl ether/ethanol. The precipitated polymer was re-dissolved in small amount of water and dialyzed twice against water in 1000 M$_w$ cut off tubing. The dialyzed solution was subsequently freeze-dried to give the white solid intermediate PVA derivative 5, 3.2%-PVA-(OCONHCH$_2$CH$_2$NHBoc)$_n$. DS 0.032. M$_w$~18175.

To the solid 3.2%-PVA-(OCONHCH$_2$CH$_2$NHBoc)$_n$ 5 (720 mg, 0.0396 mmol, 0.464 mmol of NHBoc-groups) was added TFA/water (17.5 mL, 95:5) and the mixture was shaken for 1 h at room temperature. After 1 h the reaction solution was evaporated to dryness and co-evaporated with water. The residue was re-dissolved in water and the pH was adjusted to 10 which caused complete solubilization of the material (it was poorly soluble at acidic pH). The solution was then dialyzed twice against water in 1000 M$_w$ cut off tubing, filtered, and finally freeze-dried to give 3.0%-PVA-(OCONHCH$_2$CH$_2$NH$_2$)$_n$ 6. DS 0.03. M$_w$ 16930.

General procedure for acylation of amino-modified PVA 6.

3.0%-PVA-(OCONHCH$_2$CH$_2$NH$_2$)$_n$ 6 (62.4 mg, 0.0037 mmol, 0.04 mmol of NH$_2$ groups) was dissolved in 12 mL of 10 mM Na$_2$B$_4$O$_7$ buffer (pH 8.5), while corresponding carboxylic acid NHS-ester (0.4 mmol) was dissolved in 1.5 mL of acetonitrile. These solutions were mixed by adding the reagent/acetonitrile solution to the aqueous solution of amino-modified PVA 6. The mixture was stirred overnight at room temperature. The mixture was then filtered and the filtrate was dialyzed twice against water in 1000 M$_w$ cut-off tubing, and finally freeze-dried.

Maleimidoacetyl-Derivatized PVA 7.

Amino-modified PVA 6 (135.6 mg, 0.0078 mmol, 0.123 mmol of NH$_2$ groups) and 2-maleimidoacetic acid N-hydroxysuccinimide ester (Kitagawa et al *Chem. Pharm. Bull.* 1981, 29, 1130-1135) (310.2 mg, 1.23 mmol) were used in the synthesis to give the PVA derivative 7. DS 0.044. M$_w$~19500.

Maleimidopropionyl-Derivatized PVA 8.

Amino-modified PVA 6 (62.4 mg, 0.0037 mmol, 0.04 mmol of NH$_2$ groups) and 3-maleimidopropionic acid N-hydroxysuccinimide ester (106.5 mg, 0.4 mmol) were used in the synthesis to give the PVA derivative 8. DS 0.03. M$_w$~18550.

Acrylamide-Derivatized PVA 9.

Amino-modified PVA 6 (62.4 mg, 0.0037 mmol, 0.04 mmol of NH$_2$ groups) and acrylic acid N-hydroxysuccinimide ester (67.7 mg, 0.4 mmol) were used in the synthesis to give the PVA derivative 9. DS 0.03. M$_w$~17550.

2-Iodoacetamide-Derivatized PVA 10.

Amino-modified PVA 6 (62.4 mg, 0.0037 mmol, 0.04 mmol of NH$_2$ groups) and 2-iodoacetic acid N-hydroxysuccinimide ester (Krutzsch et al *Anal. Biochem.* 1993, 209, 109-116) (113.5 mg, 0.4 mmol) were used in the synthesis to give the PVA derivative 10. DS 0.03. M$_w$~18740.

Synthesis of Maleimide-Modified PVA 11.

Amino-modified PVA 6 (61 mg, 0.0036 mmol, 0.039 mmol of NH$_2$ groups) was dissolved in 5 mL of 1M NaHCO$_3$ and the solution was treated with N-methoxycarbonylmaleimide (60.5 mg, 0.39 mmol) at 0° C. for 5 min. After 5 min the mixture was diluted with mixture of water and acetonitrile (5 mL, 1:1), and then stirred for another 1 h at room temperature. The mixture was neutralized with diluted HCl to pH 6.0 and then dialyzed against water in 1000 M$_w$ cut-off tubing. Freeze-drying of the dialyzed solution afforded the mixture of maleimide-modified PVA 11 and the imide-amide intermediate. DS=DS$_{maleimide}$+DS$_{Intermediate}$=0.012+0.018. M$_w$~17170.

Synthesis of Semicarbazide-Modified PVA 13.

Amino-modified PVA 6 (57.7 mg, 0.0034 mmol, 0.037 mmol of NH$_2$ groups) was dissolved in 12 mL of 10 mM Na$_2$B$_4$O$_7$ buffer (pH 8.5), while tert-butyl phenyl hydrazodiformate (Gray et al *Tetrahedron* 1977, 33, 739-743) (506.5 mg, 2.0 mmol) was dissolved in 2.5 mL of DMSO. These solutions were mixed by adding the reagent/DMSO solution to the aqueous solution of amino-modified PVA 6. 5 mL of acetonitrile was then added to the mixture in order to solubilize it. The mixture was stirred overnight at room temperature. It was then filtered and the filtrate was dialyzed twice against water in 1000 $M_w$ cut-off tubing, and finally freeze-dried to give the white solid Boc-protected semicarbazide PVA 12, 3.0%-PVA-(OCONHCH$_2$CH$_2$NHCONHNHBoc)$_n$. DS 0.03. $M_w$~18640.

To the solid Boc-protected semicarbazide PVA 12 (42 mg, 0.00225 mmol, 0.024 mmol of NHBoc-groups) was added TFA/water (10 mL, 95:5) and the mixture was shaken for 1 h at room temperature. After 1 h the reaction solution was evaporated to dryness and co-evaporated with water. The residue was re-dissolved in water and the pH was adjusted to 9 which caused complete solubilization of the material (it was poorly soluble at acidic pH). The solution was then dialyzed twice against water in 1000 $M_w$ cut-off tubing, filtered, and finally freeze-dried to give 3.0%-PVA-(—(OCONHCH$_2$CH$_2$NHCONHNH$_2$)$_n$ 13. DS 0.03. $M_w$~17250.

Aldehyde-modified PVA 14 and hydrazide-modified PVA 15 were prepared as previously described (Ossipov et al *J. Appl. Polym. Sci.* 2007, 106, 60-70).

Synthesis of Aldehyde-Modified HA 16.

Chemical modification of HA was carried out in aqueous conditions following previously described procedure (Jia et al *Biomacromolecules* 2006 7 3336-3344). Hyaluronic acid (500 mg, 1.34 mmol of disaccharide repeating units, Na$^+$ salt from *Streptococcus equi* with nominal molecular weight ($M_w$) 1.3 MDa (Fluka)) was dissolved in de-ionized water (100 mL), 0.5 M aqueous solution of sodium periodate (2.7 mL corresponding to 0.5 of periodate per HA repeating unit) was added dropwise, and the mixture was stirred for 2 h at room temperature in the dark. Ethylene glycol (4 equivalents) was then added to inactivate any unreacted periodate. The reaction was stirred for 1 h at ambient temperature and the solution was purified by dialysis in 25000 $M_w$ cut off tubing against water twice. The dry product was obtained by freeze-drying. The weight average molecular weight ($M_w$) of aldehyde-modified HA 16 was measured using static light scattering on a Hamamatsu photon-counting device with a 3 mW He—Ne laser. Toluene was used as a reference The amount of aldehyde groups was obtained by reaction with tert-butyl carbazate (TBC) followed by reduction with NaBH$_3$CN.

Synthesis of other HA derivatives have been done by triazine activated amidation (Bergman et al *Biomacromolecules* 8, 2190-2195 (2007)). Thus hydrazide-modified HA has been obtained by reacting triazine activated HA with tert-butylcarbazate followed by deprotection with trifluoro acetic acid (TFA), aminooxy-modified HA by reaction with N-Boc-aminooxyacetic acid hydrazide or 2-aminoethyl N-Boc-aminooxyacetamide or tert-butyl aminopropoxycarbamate followed by deprotection with TFA, amino-modified HA by reaction with N-trifluoroacetyl-1,2-ethylene diamine and removal of the TFA group, maleimide-modified HA by reaction with N-trifluoroacetyl-1,2-ethylene diamine and removal of the TFA group followed by reaction of the freed amino group with methoxycarbonyl maleimide. Aldehyde-modified HA has also been obtained via triazine-activated amidation as described for the gels used for the in vivo experiments.

Cytotoxicity of PVA Derivatives

Cells:

Human dermal fibroblasts (hDFn) were cultured in complete DME/F12 medium (Dulbecco's Modified Eagle's Medium/Nutrient Mixture F-12 Ham with L-glutamine, 15 mM HEPES and sodium bicarbonate (DME/F12) supplemented with 10% fetal bovine serum). Cells were maintained at 37° C., 5% CO$_2$ and used at passages 11 and 12.

Cytotoxicity Assay:

hDFn were seeded in 96-well plates at a 2.5×10$^4$ cells/mL density and cultured in 200 μl/well of complete DME/F12 medium at 37° C., 5% CO$_2$. After 24 hours the old medium was removed and replaced with fresh medium containing 1.7 mg/mL of the PVA derivatives 4, 13, or 15, or 13 mg/mL of the aldehyde-modified HA 16. The material was dissolved directly in cell culture medium and then passed through 0.25 μm sterile filter before being added to the cells. Fibroblasts were allowed to grow with the material at 37° C., 5% CO$_2$. Cells grown in plain cell culture medium were used as a negative control. After 0, 24 and 48 hours the MTT assay was performed to evaluate the cytotoxicity of the individual components. At each time point a 5 mg/mL solution of Thiazolyl Blue Tetrazolium Bromide (MTT) in PBS was prepared and passed through a 0.22 μm sterile filter. Thereafter, 20 μl of the MTT solution was added to each well and the plate was incubated at 37° C., 5% CO$_2$ for 3 h. Later on, the medium was carefully removed and the dark blue crystals were dissolved in 200 μl DMSO. The absorbance was measured at 570 nm and the results were compared with that of the control wells to determine relative cell viability. Decreased cell viablity in fibroblasts cultured with aldehyde-modified HA 16 could be seen already after 0 hours. The aminooxy derivatized PVA 4 showed minor cytotoxicity after 24 and 48 hours, whereas hydrazide and semicarbazide derivatized PVAs 15 and 13 had no effect on the cell viability.

Results:

Decreased cell viablity in fibroblasts cultured with aldehyde-modified HA 16 could be seen already after 0 hours. The aminooxy derivatized PVA 4 showed minor cytotoxicity after 24 and 48 hours, whereas hydrazide and semicarbazide derivatized PVAs 15 and 13 had no effect on the cell viability.

HA-PVA Hydrogel Formation and Characterization

To form the HA hydrogels cross-linked with aldehyde-reactive PVA derivatives, the solutions of aldehyde-modified HA 16 (degree of modification 4%) and corresponding PVA component were prepared in water at concentrations to give equimolar equivalents of aldehyde and hydrazide (or aminooxy, or semicarbazide) functionalities (around 25 mg/mL for HA 16 and 5 mg/mL for PVA derivative). Equal volumes of these solutions were injected using a double-barreled syringe to obtain the hydrogels with the concentration of solid contents 1.5%. Disk-shaped gels were prepared by injection of the solutions into a rubber mold sandwiched between two slide glasses. Gel formation occurred within 30 s. The obtained hydrogels were kept in the mold for 2 h to ensure complete cross-linking. The diameter and thickness of hydrogels were 20 and 3.2 mm (~1 mL).

Gel/sol fraction of the prepared disk gels were determined by swelling in de-ionized water for 24 h during which the non-incorporated network fraction (=sol fraction) was extracted. The extracted gels were stored in an open dish overnight at room temperature and then under vacuo at 37° C. to allow water evaporation and thus provide a hydratable HA hydrogel film with the mass $W_{gel}$. The dried gel was again re-swollen for 24 h in PBS buffer (pH 7.4) and weighed in air. The amount of polymer components in the soluble fraction of the gel, $W_{sol}$, was defined as the difference in weight between the initial mass of both polymer components taken for the cross-linking reaction $W_0$ and $W_{gel}$, $W_{sol}=W_0-W_{gel}$. The swelling ratio, Q, was calculated as $Q=W_s/W_{gel}$ where $W_s$ is the weight of hydrogel after swelling in PBS buffer (pH 7.4).

Storage and loss moduli (G' and G") of the prepared disk gels were measured with an AR2000 rheometer (TA Instruments Inc UK). The disks gels were immersed in PBS for 24 h and allowed to swell to equilibrium. The swollen in PBS disk gels were placed on an aluminum plate of 20 mm diameter with parallel geometry. Storage and loss moduli (G' and G") were obtained from a stress sweep (from 10 to 250 Pa) performed at the normal force of ca. 150 mN at 25° C. Data are reported at a frequency of 1.0 Hz.

Results:

Sol-to-gel transformation of the aldehyde-modified HA 16 was readily triggered by addition of PVAs modified with hydrazide, semicarbazide, or aminooxy groups due to hydrazone, semicarbazone, or oxime cross-links formation. As expected, thiol-containing PVA 1 did not afford any gel with aldehyde-modified HA but it was selectively reactive toward the maleimide-modified PVA 8 while cysteine-modified PVA 3 acted as a cross-linker for both aldehyde-modified HA due to thiozolidine cyclization and Michael addition reactions respectively. Cross-linking of the aldehyde-modified HA with different PVA derivatives gave mechanically robust hydrogels with physico-chemical properties ranging from a very soft pliable material to more elastic networks. The gel formed from aldehyde-HA 16 and cysteine-appended PVA 3, was gradually decomposing back to a clear solution in 7 days after formation. Given that thiazolidine formation is reversible the sulfhydryl groups can form disulfide bridges between the same or different molecules of cysteine-appended PVA 3 at the pH used, thus liberating the HA component from the HA/PVA network. Hydrazone cross-linked HA/PVA hydrogel showed the highest storage and loss moduli (G' and G") among all HA hydrogels that were cross-linked by aldehyde-reactive PVA derivatives. The gel fraction $W_{gel}$ for HA cross-linked with hydrazide- and aminooxy-modified PVAs were 90% and 100% respectively.

Degradation of HA-PVA Hydrogels.

Enzymatic degradation of the gels was explored. After the hydrogels were dried, they were swollen in PBS for 24 h and the swelling buffer then was diluted with HAse solution such that the final concentration of hyaluronidase was 500 U/mL. The hydrogels were then stored in PBS buffer containing HAse at room temperature for several days. Results: By the second day the oxime cross-linked hydrogel was totally degraded, while the hydrazone cross-linked hydrogel appeared totally degraded on the third day. These experiment clearly demonstrated that HAse can recognize the HA that is cross-linked with multifunctional PVA cross-linkers proposing that the prepared gels would be fully resorbable in vivo.

Cell Culture on Hydrogel Surfaces.

Hydrogels for surface cell culture were prepared by injection of filter-sterilized (0.2 μm filter) aqueous solutions (100 μl of each component, concentrations of components in solutions were made to give equimolar equivalents of reactive functionalities) through a double-barreled syringe into a round-bottom shaped 5 mL polystyrene tubes giving a final solid concentration of 1.5% (w/v). Mixed solutions were allowed to gel at room temperature for 1 h. Once polymerized each gel (0.2 mL) was covered with 4 mL of complete DME/F12 medium and incubated at 37° C. for 1 week. HDFn were seeded in 96-well plates at a $2.5 \times 10^4$ cells/mL density and cultured in 200 μl/well of complete DME/F12 medium at 37° C., 5% $CO_2$ for 24 hours. Later on, the old medium was removed and 200 μl of the medium used for gel incubation was added to the wells. The cells were allowed to grow at 37° C., 5% $CO_2$ for 0, 24 and 48 hours before performing the MTT assay according to the earlier described procedure. Fibroblasts grown in regular cell culture medium were used as a control in this study.

While the invention has been described and pointed out with reference to operative embodiments thereof, it will be understood by those skilled in the art that various changes, modifications, substitutions and omissions can be made without departing from the spirit of the invention. It is intended therefore that the invention embraces those equivalents within the scope of the claims which follow.

The invention claimed is:

1. A composition which upon activation spontaneously forms a cross-linked hydrogel in an aqueous liquid, said composition comprising:
   a) a first formulation comprising a functionalized hyaluronan (HA) comprising an HA-backbone and a plurality of HA-reactive substituent groups directly attached to said HA-backbone, said substituent group comprising a reactive functional HA-group, wherein the degree of substitution (DS) measured as number of reactive HA-substituents per repeating unit is ≤20%, and
   b) a second formulation comprising a homo-multifunctional cross-linking reagent of a polyhydroxy polymer (PHP) comprising a PHP-backbone and a plurality of PHP-reactive substituent groups attached to said PHP-backbone, said substituent group comprising one or more reactive functional PHP-groups,
   wherein said PHP-backbone comprises one or more linear structures selected from the group consisting of:
   (i) linear polyamide backbones of identical or different monomeric subunits linked together one after the other with an amide bond (—$CONR'_1$—) linking two neighboring subunits together, and with corresponding monomers selected from amino carboxylic acids or combinations of a diamine with a dicarboxylic acid;
   (ii) linear polyester backbones of identical or different monomeric subunits with an ester bond (—COO—) linking two neighboring subunits together, and with corresponding monomers selected from hydroxy carboxylic acids or combinations of a dialcohol with a dicarboxylic acid;
   (iii) linear polyether backbones of identical or different monomeric alkylene oxide subunits with an ether bond (—O—) linking two neighboring subunits together and a straight alkylene chain linking neighboring ether groups together, with the proviso that the chain comprises ≥2 carbons, and with corresponding monomers selected from alkylene oxides; and
   (iv) linear polyvinyl backbones of identical or different monomeric $C_2$-alkylene chain subunits —($CH_2$—$CH_2$—);
   said reactive HA and PHP groups being selected as a pair of counterparts that are capable of mutually and selectively reacting with each other to form a covalent linkage structure,
   A) a first counterpart of said pair comprises a nucleophilic group and a second counterpart of the same pair comprises an electrophilic group,
   said nucleophilic groups being selected from the group consisting of: carbazate groups, hydrazide groups, semicarbazide groups, thiosemicarbazide groups, aminooxy groups, thiol groups, and β-aminothiol groups, and
   said electrophilic groups being selected from the group consisting of: aldehyde groups, maleimide groups, acrylate groups, acrylamide groups, methacrylate groups, methacrylamide groups, vinylsulphone groups, and aziridinyl groups, or B) the two counterpart groups of said pair are counterpart reactants capable of reacting with each other in a cycloaddition reaction, and wherein said hydrogel has a cross-linking structure which is attached to said hyaluronan via two or more of said linkage structure and defined by said cross-linking reagent, and wherein said cross-linking structure exhibits a plurality of hydroxyl groups.

2. The composition of claim 1, wherein said reactive HA-group and said reactive PHP-group are capable of forming said linkage structure in a reaction sequence comprising a substitution reaction step and/or an addition reaction step with either of the two steps preceding the other.

3. The composition of claim 1, wherein at least one reactive HA-substituent is replacing a carboxy group of native hyaluronic acid.

4. The composition of claim 1 wherein
said PHP-backbone comprises a linear structure of ≥5 monomeric units, and/or
said PHP-polymer comprises ≥5 hydroxyl groups.

5. The composition of claim 1, wherein said PHP-backbone structure comprises a linear polyvinyl backbone structure.

6. The composition of claim 1, wherein said hyaluronan, said cross-linking reagent, and the conditions provided by said aqueous liquid have been selected to match each other, enabling spontaneous cross-linking and hydrogel formation within ≤15 minutes from activation of the composition.

7. The composition of claim 1, wherein the ratio between molar amount of the reactive HA-group ($M_{HA}$) in said first formulation and the molar amount of the reactive PHP-group ($M_{PHP}$) in said second formulation is 0.1-10.

8. The composition of claim 1, wherein the hyaluronan and the cross-linking reagent have been selected so that the hydrogel formed as a consequence of activation and cross-linking is biocompatible.

9. The composition according to claim 1, further comprising particles dispersible in said aqueous liquid, and/or a bioactive substance.

10. The composition of claim 1, wherein said cross-linking reagent comprises ≥5 of said plurality of hydroxyl groups.

11. The composition of claim 1, wherein said cross-linking reagent comprises ≥10 of said plurality of hydroxyl groups.

12. The composition of claim 1, wherein said hyaluronan, said cross-linking reagent, and the conditions provided by said aqueous liquid have been selected to match each other enabling spontaneous cross-linking and hydrogel formation within ≤1 minute from activation of the composition.

13. The composition of claim 1, wherein
said hyaluronan is soluble in said aqueous liquid and the degree of substitution for said reactive HA-substituent measured as relative amount of repetitive units that carry a reactive HA-substituent/group is ≤20%, and
the cross-linking reagent is soluble in said aqueous liquid and the degree of substitution measured as relative amount of repeating units that carry a reactive PHP-substituent/group is ≤20%.

14. The composition of claim 1, wherein the degree of substitution measured as number of reactive HA-substituents per repeating unit is less than 10%.

15. The composition of claim 1, wherein the degree of substitution measured as number of reactive PHP-substituents per repeating unit is less than 10%.

16. The composition of claim 1, wherein the ratio between molar amount of the reactive HA-group ($M_{HA}$) in said first formulation and molar amount of the reactive PHP-group ($M_{PHP}$) in said second formulation is 0.75-1.30.

17. The composition of claim 1, further comprising a buffer system that provides a physiologically acceptable pH in the aqueous liquid in which the cross-linking reaction and hydrogel formation are to take place.

18. The composition of claim 1, wherein said first formulation and said second formulation are each contained in a separate compartment of a compartmentalized vehicle.

19. The composition of claim 1, wherein the PHP comprises a linear polyvinyl backbone and reactive substituent groups selected from the group consisting of thiol, β-aminothiol, aminooxy, maleimide, semicarbazide, aldehyde and hydrazide groups.

20. The composition of claim 1, wherein the HA comprises reactive aldehyde substituent groups.

21. The composition of claim 1, wherein the PHP comprises a linear polyvinyl backbone and reactive hydrazide substituent groups, and the HA comprises reactive aldehyde substituent groups.

* * * * *